US010736525B2

(12) United States Patent
Cardenas et al.

(10) Patent No.: US 10,736,525 B2
(45) Date of Patent: Aug. 11, 2020

(54) SYSTEMS AND METHODS FOR CHARACTERIZATION OF SEIZURES

(71) Applicant: Brain Sentinel, Inc., San Antonio, TX (US)

(72) Inventors: Damon P. Cardenas, San Antonio, TX (US); Jose E. Cavazos, San Antonio, TX (US); Michael R. Girouard, San Antonio, TX (US); Jonathan J. Halford, Mount Pleasant, SC (US); Luke E. Whitmire, San Antonio, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 333 days.

(21) Appl. No.: 15/491,883

(22) Filed: Apr. 19, 2017

(65) Prior Publication Data
US 2017/0296083 A1    Oct. 19, 2017

Related U.S. Application Data

(60) Provisional application No. 62/324,786, filed on Apr. 19, 2016.

(51) Int. Cl.
*A61B 5/04* (2006.01)
*A61B 5/0488* (2006.01)
*A61B 5/00* (2006.01)

(52) U.S. Cl.
CPC ........ *A61B 5/04014* (2013.01); *A61B 5/0488* (2013.01); *A61B 5/4094* (2013.01); *A61B 5/726* (2013.01); *A61B 5/7264* (2013.01)

(58) Field of Classification Search
None
See application file for complete search history.

(56) References Cited

U.S. PATENT DOCUMENTS

| | | | |
|---|---|---|---|
| 3,815,611 | A | 6/1974 | Denniston, III |
| 4,197,856 | A | 4/1980 | Northrop |
| 4,566,464 | A | 1/1986 | Piccone et al. |
| 4,878,498 | A | 11/1989 | Abrams et al. |
| 5,263,489 | A | 11/1993 | Johnson et al. |

(Continued)

FOREIGN PATENT DOCUMENTS

| | | |
|---|---|---|
| EP | 2123221 | 11/2009 |
| WO | WO2004066832 | 8/2004 |

(Continued)

OTHER PUBLICATIONS

Conradsen, et al., "Evaluation of novel algorithm embedded in a wearable sEMG device for seizure detection," 34th Annual International Conference of the IEEE EMBS, San Diego, California, USA, Aug. 28-Sep. 1, 2012, pp. 2048-2051.

(Continued)

*Primary Examiner* — Michael R Bloch
(74) *Attorney, Agent, or Firm* — Pizarro Allen PC

(57) ABSTRACT

Systems and methods are described for detecting and characterizing seizures or seizure-related events. The methods herein may include determining magnitude and/or scaled magnitude data for each of at least one high and low frequency group of signals. Based on the determined magnitudes and/or scaled magnitude data, seizures or seizure-related events may be characterized.

16 Claims, 13 Drawing Sheets

(56) References Cited

U.S. PATENT DOCUMENTS

| | | | |
|---|---|---|---|
| 5,269,302 | A | 12/1993 | Swartz et al. |
| 5,301,680 | A | 4/1994 | Rosenberg |
| 5,311,876 | A | 5/1994 | Olsen et al. |
| 5,349,962 | A | 9/1994 | Lockard et al. |
| 5,373,852 | A | 12/1994 | Harrison et al. |
| 5,743,860 | A | 4/1998 | Hively et al. |
| 5,769,778 | A | 6/1998 | Abrams et al. |
| 5,810,747 | A | 9/1998 | Brudny et al. |
| 5,871,517 | A | 2/1999 | Abrams et al. |
| 5,879,309 | A | 3/1999 | Johnson et al. |
| 5,959,529 | A | 9/1999 | Kail, IV |
| 5,995,868 | A | 11/1999 | Dorfmeister et al. |
| 6,016,449 | A | 1/2000 | Fischell et al. |
| 6,018,682 | A | 1/2000 | Rise |
| 6,238,338 | B1 | 5/2001 | Deluca et al. |
| 6,315,740 | B1 | 11/2001 | Singh |
| 6,440,067 | B1 | 8/2002 | DeLuca et al. |
| 6,471,087 | B1 | 10/2002 | Shusterman |
| 6,473,639 | B1 | 10/2002 | Fischell et al. |
| 6,549,804 | B1 | 4/2003 | Osorio et al. |
| 6,597,944 | B1 | 7/2003 | Hadas |
| 6,643,541 | B2 | 11/2003 | Mok et al. |
| 6,678,549 | B2 | 1/2004 | Cusimano et al. |
| 6,819,956 | B2 | 11/2004 | DiLorenzo |
| 6,950,688 | B2 | 9/2005 | Axelgaard et al. |
| 7,024,247 | B2 | 4/2006 | Gliner et al. |
| 7,160,252 | B2 | 1/2007 | Cho et al. |
| 7,188,151 | B2 | 3/2007 | Kumar et al. |
| 7,209,787 | B2 | 4/2007 | DiLorenzo |
| 7,231,254 | B2 | 6/2007 | DiLorenzo |
| 7,242,984 | B2 | 7/2007 | DiLorenzo |
| 7,277,758 | B2 | 10/2007 | DiLorenzo |
| 7,539,533 | B2 | 5/2009 | Tran |
| 8,386,025 | B2 | 2/2013 | Hoppe |
| 8,983,591 | B2 | 3/2015 | Leininger et al. |
| 9,186,105 | B2 | 11/2015 | Leininger et al. |
| 10,420,499 | B2 * | 9/2019 | Conradsen ............ A61B 5/7246 |
| 2002/0177882 | A1 | 11/2002 | DiLorenzo |
| 2003/0109905 | A1 | 6/2003 | Mok et al. |
| 2003/0236474 | A1 | 12/2003 | Singh |
| 2005/0081847 | A1 | 4/2005 | Lee et al. |
| 2005/0277844 | A1 | 12/2005 | Strother et al. |
| 2006/0004299 | A1 | 1/2006 | Endo et al. |
| 2006/0025697 | A1 | 2/2006 | Kurzweil et al. |
| 2007/0150024 | A1 | 6/2007 | Leyde et al. |
| 2007/0204691 | A1 | 9/2007 | Bogner et al. |
| 2007/0208212 | A1 | 9/2007 | DiLorenzo |
| 2007/0208263 | A1 | 9/2007 | John et al. |
| 2007/0287931 | A1 | 12/2007 | DiLorenzo |
| 2008/0001735 | A1 | 1/2008 | Tran |
| 2008/0005838 | A1 | 1/2008 | Wang Fong et al. |
| 2008/0077039 | A1 | 3/2008 | Donnett et al. |
| 2008/0082019 | A1 | 4/2008 | Ludving et al. |
| 2008/0091089 | A1 | 4/2008 | Guillory et al. |
| 2008/0091090 | A1 | 4/2008 | Guillory et al. |
| 2008/0146958 | A1 | 6/2008 | Guillory et al. |
| 2009/0054737 | A1 | 2/2009 | Magar et al. |
| 2009/0137921 | A1 | 5/2009 | Kramer et al. |
| 2010/0013773 | A1 | 6/2010 | Hoppe |
| 2010/0198098 | A1 | 8/2010 | Osorio et al. |
| 2012/0083700 | A1 | 4/2012 | Osorio |
| 2012/0108999 | A1 * | 5/2012 | Leininger ............ A61B 5/0004 600/546 |
| 2012/0197092 | A1 * | 8/2012 | Luo ............ A61B 5/0478 600/301 |
| 2012/0283526 | A1 | 11/2012 | Gommesen et al. |
| 2012/0310050 | A1 | 12/2012 | Osorio |
| 2013/0012830 | A1 * | 1/2013 | Leininger ............ A61B 5/0488 600/546 |
| 2013/0041275 | A1 * | 2/2013 | Syed ............ A61B 5/0456 600/521 |
| 2013/0060167 | A1 * | 3/2013 | Dracup ............ A61B 5/11 600/595 |
| 2013/0116514 | A1 * | 5/2013 | Kroner ............ A61B 5/01 600/301 |
| 2014/0163413 | A1 | 6/2014 | Conradsen et al. |
| 2014/0202098 | A1 | 7/2014 | De Smet et al. |
| 2015/0119746 | A1 | 4/2015 | Conradsen |
| 2015/0250415 | A1 | 10/2015 | Leininger et al. |

FOREIGN PATENT DOCUMENTS

| | | |
|---|---|---|
| WO | WO2006008334 | 1/2006 |
| WO | WO2006094513 | 9/2006 |
| WO | WO2006134359 | 12/2006 |
| WO | WO2007034476 | 3/2007 |
| WO | WO2007142523 | 12/2007 |
| WO | WO2008057365 | 5/2008 |
| WO | WO2008131782 | 11/2008 |
| WO | WO2011072684 | 6/2011 |
| WO | WO2012051628 | 4/2012 |
| WO | WO2013006728 | 1/2013 |
| WO | WO2015035413 | 3/2015 |
| WO | WO 2015/084899 | 6/2015 |

OTHER PUBLICATIONS

Conradsen, et al., "Seizure Onset Detection based on a Uni- or Multi-modal Intelligent Seizure Acquisition (UISA/MISA) System," 32nd Annual International Conference of the IEEE EMBS Buenos Aires, Argentina, Aug. 31-Sep. 4, 2010, pp. 3269-3272.

Conradsen, et al., "Dynamics of muscle activation during tonic-clonic seizures," Epilepsy Research, vol. 104, Issues 1-2, Mar. 2013, pp. 84-93.

Sandor Beniczky, et al., "Quantitative analysis of surface electromyography during epileptic and nonepileptic convulsive seizures," Epilepsia, vol. 55, Issue 7, Jul. 2014, pp. 1128-1134.

Rens Wientjes, "Potential Value of Surface Electromyography for Automated Epileptic Seizure Detection for Children in a Home Monitoring System," Eindhoven University of Technology Department of Electrical Engineering Signal Processing Systems, Master of Science Thesis, Project Period May 2006-Aug. 2007, Report 1107, pp. 1-101.

Conradsen, et al., "Patterns of Muscle Activation During Generalized Tonic and Tonic-Clonic Epileptic Seizures," Wiley Periodicals, Inc., 2011 copyright International League Against Epilepsy, pp. 1-8.

Conradsen, et al., "Multi-Modal Intelligent Seizure Acquisition (MISA) System—A New Approach Towards Seizure Detection Based on Full Body Motion Measures," 31st Annual International Conference of the IEEE EMBS Minneapolis, Minnesota, USA, Sep. 2-6, 2009, pp. 2591-2595.

Uri Kramer, et al., "A Novel Portable Seizure Detection Alarm System: Preliminary Results," Journal of Clinical Neurophysiology, vol. 28, No. 1, Feb. 2011, pp. 36-38.

Kris Cuppens, et al., "Detection of Nocturnal Frontal Lobe Seizures in Pediatric Patients by Means of Accelerometers: A First Study," 31st Annual International Conference of the IEEE EMBS, Minneapolis, Minnesota, USA, Sep. 2-6, 2009, pp. 6608-6611.

Dutch Epilepsy Clinics Foundation Automates the Detection and Diagnosis of Epileptic Seizures with Simulink and the Video and Image Processing Blockset, www.mathworks.com, 91399v00 Jun. 2006 (2 pages), Page Accessed, Jun. 2006.

Epilepsy Detector Application, http://www.epdetect.com/index.html (6 pages), Page accessed, Sep. 2009.

"Medpage ST-2; Movement Sensor Epileptic Seizure Monitor Alarm System with Breathing Monitor Alarm," http://wwww.medpage-ltd.com/page65.html (6 pages), Page accessed Sep. 2009.

"NeuroPace—Product," http://www.neuropace.com/product/overview.html (2 pages), Page accessed Sep. 2009.

NeuroVista, http://www.neurovista.com/research.html (1 page), Page accessed, Sep. 2009.

"Standards for Reporting Electromyography Data," Journal of Athletic Training, available at http://www.nata.org/jat/authors/electromyography_data.htm (4 pages). First Published 1996.

(56) References Cited

OTHER PUBLICATIONS

B. Bigland-Ritchie, et al., "Muscle Temperature, Contractile Speed, and Motoneuron Firing Rates During Human Voluntary Contractions," The American Physiological Society 0161-7567/92, 1992, pp. 2457-2461.

B. Bigland-Ritchie, et al., "Conduction Velocity and EMG Power Spectrum Changes in Fatigue of Sustained Maximal Efforts," The American Physiological Society 0161/7567/81/0000-0000, 1981, pp. 1300-1305.

Juliana Lockman, et al., "Detection of Seizure-Like Movements Using a Wrist Accelerometer," Epilepsy & Behavior 20 (2011) 638-641.

Conradsen et al., "Automatic Multi-modal intelligent seizure acquisition (MISA) system for detection of motor seizures from electromyographic data and motion data," Computer Methods and Programs in Biomedicine 107 (2012) 97-110 (14 Pages).

Poh et al., "Convulsive Seizure Detection Using a Wrist-Worn Electrodermal Activity and Accelerometry Biosensor" Epilepsia, 53(5) e93-e97 (2012) (5 Pages).

Jean_Marc Le Caillec, Rene Garello "Comparison of Statistical Indices using Third Order Statistics for Nonlinearity Detection" in Signal Processing, vol. 84, Issue 3, Mar. 2004, pp. 499-525. (26 Pages).

Xue Wang, Yonghong Chen, "Testing for Statistical Significance in Bispectra: A Surrogate Data Approach and Application to Neuroscience" in IEEE Transactions on Biomedical Engineering, vol. 54, No. 11, Nov. 2007, pp. 1974-1982. (9 pages).

A. Dahaba et al. "Bispectral Index (BIS) monitoring of acute encephalitis with refractory, repetitive partial seizures (AERRPS)" in Minerva Anestesiologica, Apr. 2010 pp. 298-201. (4 pages).

K. Chua et al. "Application of higher order statistics/spectra in biomedical signals—A review" in Medical Engineering & Physics vol. 32 Issue 7, Sep. 2010 pp. 679-689. (11 pages).

N. Thakor and S. Tong "Advances in Quantitative Electroencephalogram Analysis Methods" in Annu. Rev. Biomed. Eng. vol. 6 Apr. 2004 pp. 453-495. (48 pages).

Muthuswamy et al. "Higher-Order Spectral Analysis of Burst Patterns in EEG" in IEEE Transactions in Biomedical Engineering, vol. 46, No. 1, Jan. 1999. (8 pages).

International Search Report and Written Opinion dated Jan. 25, 2013 in PCT Pat. App. No. PCT/US14/54837.

International Search Report and Written Opinion dated Jul. 20, 2017 in International Patent Application No. PCT/US2017/028429 (8 pages).

Sigge NL et al. "Detection of Tonic Epileptic Seizures Based on Surface Electromyography," 2014 36th Annual International Conference on IEEE Engineering in Medicine and Biology Society, IEEE, Aug. 26, 2014 (Aug. 26, 2014), pp. 942-945, XP032675231. (4 Pages).

Kanemoto et al. "PNES around the world: Where we are now and how we can close the diagnosis and treatment gaps—an ILAE PNES Task Force report." Epilepsia Open, 2017, 2 (3): 307-316 (10 pages).

Reuber et al. "Diagnostic Delay in Psychogenic Nonepilpetic Seizures," Neurology, 2002 pp. 493-495 (3 pages).

Larsen et al. "Detection of Tonic Epileptic Seizures Based on Surface Electromyography," 2014 IEEE, 36th Annual International Conference of the IEEE Engineering in Medicine and Biology Society, Aug. 26, (Aug. 26, 2014) pp. 942-945 (4 pages).

* cited by examiner

SYSTEMS AND METHODS FOR CHARACTERIZATION OF SEIZURES

CROSS-REFERENCE TO RELATED APPLICATION

This application claims priority to U.S. Provisional Patent Application No. 62/324,786 filed Apr. 19, 2016, the disclosure of which is herein incorporated by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system activating different muscles of the body. Other seizure events, such as psychogenic or non-epileptic seizures (PNES) may be characterized by abnormal muscle movements, but may not necessarily involve the same type of asynchronous brain activity as may more common seizure events.

Techniques designed for studying and monitoring seizures have typically relied upon electroencephalography (EEG), which characterizes electrical signals using electrodes attached to the scalp or head region of a seizure-prone individual or seizure patient. In EEG, electrodes may be positioned so as to measure such activity; that is, electrical activity originating from neuronal tissue. Alternatively, electromyography (EMG) may be used for seizure detection. In EMG, an electrode may be placed on or near the skin, over a muscle, to detect electrical activity resulting from muscle fiber activation.

Detecting an epileptic seizure using EEG typically requires attaching many electrodes and associated wires to the head and using amplifiers to monitor brainwave activity. The multiple EEG electrodes may be very cumbersome and generally require some technical expertise to apply and monitor. Furthermore, confirming a seizure may require observation in an environment provided with video monitors and video recording equipment. Unless used in a staffed clinical environment, such equipment may not be intended to determine if a seizure is in progress, but rather provide a historical record of the seizure after the incident. Such equipment is usually meant for hospital-like environments where a video camera recording or caregiver's observation may provide corroboration of the seizure and is typically used as part of a more intensive care regimen such as a hospital stay for patients who experience multiple seizures.

Even when monitoring a patient using EEG and the patient's environment with video recording, it may be difficult to characterize all types of seizure-related events that a patient may experience. For example, although specialized caregivers or epileptologists may sometimes be able to differentiate between some types of seizures which may result from epilepsy, such as generalized tonic-clonic (GTC) seizures, and other types of related events, such as PNES events, missed or inaccurate diagnosis may still occur. Additionally, other caregivers, who may not have the same level of expertise and training as specialized epileptologists, generally cannot identify differences between GTC and PNES seizures. This is particularly troubling because delayed or incorrect diagnosis of PNES may be costly to hospitals, and incorrect or incomplete diagnosis may prevent patients from receiving proper care. Accordingly, methods designed to verify and/or assist caregivers in making a proper diagnosis of epilepsy and/or other related conditions would be extremely useful.

Ambulatory devices for diagnosis of seizures may also be primarily EEG-based, but because of the above shortcomings those devices are not designed or suitable for long-term home use or daily wearability. Other seizure alerting systems may operate by detecting motion of the body, usually the extremities. Such systems may generally operate on the assumption that while suffering a seizure, a person will move erratically and violently. For example, accelerometers may be used to detect violent extremity movements. However, depending upon the type of seizure, this assumption may or may not be true. Electrical signals sent from the brain during some seizures may be transmitted to many muscles simultaneously, which may result in muscles fighting each other and effectively canceling out violent movement. In other words, the muscles may work to make the person rigid rather than cause actual violent movement. Thus, some seizures may not be consistently detected with accelerometer-based detectors.

Ambulatory devices for diagnosis of seizures are generally not suited to grade seizures based on intensity, nor are they suited to differentiate seizure-related signals based on event type. Rather, different types of seizures may often be grouped together. For example, suitable methods for characterization of data collected using ambulatory devices and for generating statistical information useful to caregivers are noticeably deficient or missing.

Accordingly, there is a need for epileptic seizure detection methods and apparatuses that can be used in non-institutional or institutional environments without many of the cumbersome electrodes to the head or extremities. There is further a need for detection methods that are suited to analyze seizures by type and/or intensity in order to characterize seizure events to help medically and surgically manage patient care. For example, robust methods for differentiating GTC seizures from PNES seizures may greatly improve patient care. There is further a need for methods that are suited to characterize seizures using automated or semi-automated algorithms including ones that may be used to rapidly search through and characterize extensive patient data, such as may be produced from personal mobile devices. There is further a need for systems and methods useful in aiding caregivers in making and/or verifying a proper diagnosis of epilepsy and/or other related conditions.

SUMMARY

In some embodiments, a method of analyzing an EMG signal for characteristics of seizure activity may include receiving EMG signal data for analysis; selecting data for a seizure-related event included among the EMG signal data; transforming the data for the seizure-related event using one or more wavelet transforms in order to produce transformed data for the seizure-related event; organizing the transformed data for the seizure-related event into one or more high frequency groups of EMG signal data and one or more low frequency groups of EMG signal data; wherein the one or more high frequency groups of EMG signal data includes data for a band of frequencies from about 120 Hz to about 400 Hz; wherein the one or more low frequency groups of EMG signal data includes data for a band of frequencies from about 6 Hz to about 70 Hz; determining magnitude data for each of the one or more high frequency groups of EMG signal data and the one or more low frequency groups of EMG signal data; scaling the magnitude data for each of the one or more high frequency groups of EMG signal data and the one or more one low frequency groups of EMG signal data in order to produce scaled magnitude data for the one or more high frequency groups of EMG signal data and scaled magnitude data for the one or more low frequency groups of EMG signal data; wherein scaling the magnitude data includes dividing the magnitude data for each of the one or more high frequency groups of EMG signal data and the one or more low frequency groups of EMG signal data by a maximum magnitude value; comparing the scaled magnitude data for the one or more high frequency groups of EMG signal data to one or more thresholds in order to detect tonic phase seizure activity; comparing the scaled magnitude data for said one or more low frequency groups of EMG signal data to one or more thresholds in order to detect clonic phase seizure activity; classifying the seizure-related event based on the presence of the tonic phase seizure activity, the clonic phase seizure activity or both; and reporting a result for the classification of the seizure-related event to one or more caregivers.

In some embodiments, a method for detecting a PNES seizure event and differentiating the PNES seizure event from GTC seizures may include receiving EMG signal data for analysis; selecting data for a seizure-related event included among the EMG signal data; transforming the data for the seizure-related event using one or more wavelet transforms in order to produce transformed data for the seizure-related event; organizing the transformed data for the seizure-related event into a high frequency group of EMG signal data and a low frequency group of EMG signal data; wherein the high frequency group of EMG signal data includes data for a band of frequencies from about 120 Hz to about 400 Hz; wherein the low frequency group of EMG signal data includes data for a band of frequencies from about 6 Hz to about 70 Hz; determining magnitude data for each of the high frequency group of EMG signal data and the low frequency group of EMG signal data; determining integrated areas for each of the magnitude data for the high frequency group of EMG signal data and the magnitude data for the low frequency group of EMG signal data; determining one or more ratios between the integrated areas; determining if the one or more ratios meets a threshold ratio condition; and classifying the seizure-related event as either of a PNES seizure event or GTC seizure based on whether the threshold ratio condition is met.

DETAILED DESCRIPTION

Figure 1:
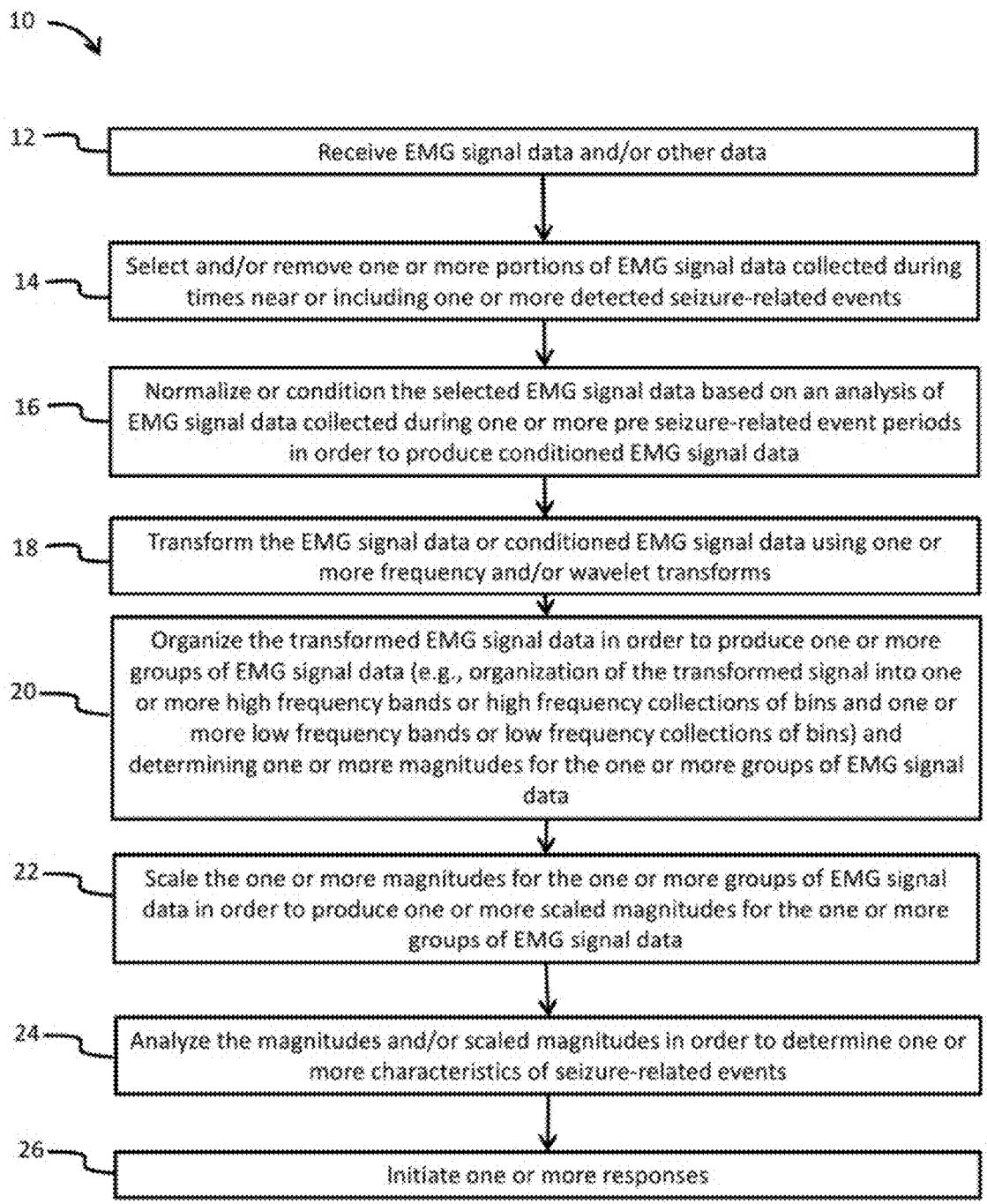
FIG. 1 is a flowchart showing some embodiments of a method for characterizing EMG signal data.

The following terms as used herein should be understood to have the indicated meanings.

When an item is introduced by "a" or "an," it should be understood to mean one or more of that item.

The term "binning" as used herein means a process of organizing EMG signal data by creating one or more bins of EMG signal data.

"Comprises" means includes but is not limited to.

"Comprising" means including but not limited to.

"Computer" means any programmable machine capable of executing machine-readable instructions. A computer may include but is not limited to a general purpose computer, microprocessor, computer server, digital signal processor, or a combination thereof. A computer may comprise one or more processors, which may comprise part of a single machine or multiple machines.

The term "computer program" means a list of instructions that may be executed by a computer to cause the computer to operate in a desired manner.

The term "computer readable medium" means a tangible article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

The term "designated EMG seizure data" as used herein means EMG signal data identified by one or more caregivers as being associated with one or more seizures. For example, a caregiver may identify EMG signal data as related to a seizure based on EEG data, video data, other data, and/or combinations thereof. EMG signal data for a seizure event included among designated EMG seizure data may be referred to as a designated EMG seizure event.

The term "detection" as used herein means identifying the presence of something. For example, detection of a seizure-related event may refer to the identification of a seizure-related event in a portion of a collected EMG signal. Where reference is made to detection of a seizure-related event, such may refer to the identification of a seizure-related event in one or more collected signals. Detection of seizure-related events may include use of signals collected and processed in real-time, signals analyzed following collection in a post-process routine, or both. Where detection is particularly limited to detection made in real-time the term "real-time detection" may be used.

"Having" means including but not limited to.

The term "seizure event" refers to a clinical episode where the patient experiences any of various types of epileptic seizures, seizures associated with a seizure disorder, psychogenic or non-epileptic seizures (PNES), or other seizures.

The term "seizure-detection routine" refers to a method or part of a method that may be used to monitor a patient for seizure-related muscle activity. A seizure-detection routine may be run individually in a strategy for monitoring a patient or may be run in combination with other seizure-detection routines or methods in an overall strategy for patient monitoring. For example, a processor may execute a seizure-detection routine configured to process an EMG signal in order to calculate one or more values of one or more measurable properties of the EMG signal and compare the one or more properties to one or more thresholds in order to detect one or more seizure-related events.

The term "seizure-related muscle activity" as used herein refers to muscle activity that exhibits a measurable property detectable using EMG that is increased or more prevalent during any of various types of epileptic seizures, seizures associated with a seizure disorder, psychogenic or non-epileptic seizures (PNES), or other seizures when compared to one or more levels of the property measured for a patient at rest and in a normal or non-seizure state. Included among measurable properties that may be increased or may become more prevalent during the aforementioned seizures are levels of overall muscle activity, coherence of muscle groups, levels of rhythmic or repetitive muscle activation, other properties associated with the aforementioned seizures, and combinations thereof. While some measurable properties using EMG may be more prevalent when a seizure is occurring, those properties may also be present or elevated, at least to some degree, during some non-seizure activities. Accordingly, as used in this disclosure, measured or detected seizure-related muscle activity may or may not be indicative of an actual seizure or epileptic seizure.

The term "seizure-related event" as used herein means a clinical episode or event in which a patient exhibits seizure-related muscle activity. A seizure-related event may or may not be associated with an actual seizure or epileptic seizure.

Where a range of values is described, it should be understood that intervening values, unless the context clearly dictates otherwise, between the upper and lower limit of that range and any other stated or intervening value in other stated ranges, may be used within embodiments described herein.

The systems and methods described herein may be used to detect and/or characterize seizures or seizure-related events. In some embodiments, the systems and methods described herein may be configured for real-time monitoring of patients and may be used to timely alert caregivers of seizure-related events and/or update an alert response. In other embodiments, methods described herein may be used to characterize or analyze historical or earlier collected data including, for example, patient data collected using one or more EMG sensors and/or other sensors. In some embodiments, systems and methods herein may be used to verify or assist a caregiver in making a diagnosis. For example, systems and methods herein may be used to assist a caregiver in making a diagnosis that a patient is experiencing PNES events and may not have epilepsy. The apparatuses described herein may include sensors including one or more electrodes disposed on, near, or underneath the skin of a patient (e.g., implanted electrodes may be used with some patients) or attached to a patient's clothing and may be configured for measurement of muscle electrical activity. In some embodiments, apparatuses and methods described herein may exclude, or exclude use of, a detection sensor, but may include, or include use of, one or more processors suitably configured to receive EMG signal data or other sensor signal data and process the data to detect and/or characterize a seizure event or seizure-related event data. Detection of seizures is further described in, for example, Applicant's U.S. Pat. Nos. 8,983,591, 9,186,105, 9,439,595, and 9,439,596 and Applicant's U.S. patent application Ser. Nos. 13/542,596, 14/816,924, and 14/920,665 and Applicant's International Applications PCT/US14/61783, PCT/US14/68246, PCT/US15/00475, PCT/US15/49859 and PCT/US16/28005, and Applicant's U.S. Provisional Patent Application Nos. 61/875,429, 61/894,793, 61/910,827, 61/969,660, 61/979,225, 62/001,302, 62/032,147, 62/050,054, 62/096,331, 62/429,359, 62/324,786, and 62/485,268, the disclosures of each of which are herein fully incorporated by reference.

In some embodiments, EMG signals may be processed and used or included in methods to determine values of one or more characteristics of seizure events or seizure-related events, which may, for example, be included in a quantitative summary of characteristics of event activity. That information may then be provided to one or more caregivers. For example, a quantitative summary of characteristics of a detected seizure may be created and may include, by way of nonlimiting example, the duration of phases or parts of the seizure, including the tonic phase, clonic phase, entire seizure, and any combinations thereof. In some embodiments, the intensity or normalized intensity of one or more phases of a seizure or of an entire seizure may also be determined and may be included in a summary provided to one or more caregivers. In some embodiments, other characteristics associated with seizure events or seizure-related events, including, for example, characteristics of samples of EMG signal including elevated amplitude qualified as being related to clonic-phase activity, such as described in Applicant's copending U.S. application Ser. No. 14/920,665, may also be determined. For example, methods and routines described herein, whether explicitly or through incorporation by reference, may sometimes be executed together with other methods or routines which may be suitable to count qualified samples and to provide a statistical summary of qualified samples to one or more caregivers. For example, in some embodiments, transition times into and/or out of one or more phases of a seizure may be determined using methods herein, and those transition times may be used to organize or verify burst data (e.g., such as to link burst data to the clonic phase) so that appropriate burst data is properly linked to the clonic phase and may be more accurately counted and/or characterized in some other way.

Seizure events or seizure-related events that may be detected herein include generalized tonic-clonic seizure (GTC) events which may be caused by epilepsy. However, some of the embodiments described herein may also be used to detect other types of seizure-related events including, for example, some that may result from conditions other than epilepsy. For example, some seizures that may share one or more characteristics with generalized tonic-clonic seizures commonly associated with epilepsy, such as increased muscle activity or increased repetitive muscle activity, may also be detected. For example, in some embodiments, PNES events, which may be associated with conditions other than epilepsy, may be detected. Accordingly, PNES events may be detected and used to indicate that a patient may have a condition other than epilepsy. In some embodiments, such as where detection units may be disposed on more than one location or side of a patient's body, complex-partial seizures may also be detected.

In some embodiments, methods described herein may analyze muscle activity for frequency components of muscle activity that may change during the course of a seizure. For example, methods herein may collect EMG signals and process the signals to detect one or more high frequency components of an EMG signal, including signals above about 100 Hz. Methods herein may further process signals to detect one or more low frequency components of an EMG signal, including signals less than about 75 Hz. In some embodiments, low frequency components of muscle activity may be monitored that may sometimes be indicative of muscle fatigue and/or of changes in a distribution of muscle fibers that may relate to transition between the tonic and clonic phases of a seizure. For example, in some embodiments, EMG signals may be collected and processed to identify frequency components between about 20 Hz to about 75 Hz. In some embodiments, low frequency components of EMG signal typically associated with repetitive motion of extremities, which may be identified during parts of the clonic phase of a seizure, may sometimes be excluded from one or more frequency bands used to indicate transition between the tonic and clonic phases of a seizure. For example, in some embodiments, frequency bands less than about 20 Hz or less than about 10 Hz may sometimes be excluded from one or more frequency bands. Accordingly, low frequency sources of noise, which may sometimes be difficult to fully remove or discriminate from muscle activity manifesting at frequencies less than about 10 Hz, may be avoided or removed with high efficiency. High sensitivity detection or prediction of transition into the clonic phase of a seizure may then be made and/or made with minimal temporal lag between detection of phase transition and physical manifestation of the transition. Some embodiments where early detection or prediction is made of a transition into the clonic phase of a seizure may, for example, be used in methods or systems used to treat or attenuate a seizure or in methods or systems where collection of data using one or more sensors or activation of other devices is gated or initiated based on seizure detection.

In some embodiments, wavelet and/or other processing as described herein may be used to transform signal data in order to configure the data for detection of data features that may manifest over different frequencies and/or over different time scales. In some embodiments, one or more wavelet or other transforms may be used to transform EMG signal data to a form suitable for processing in order to detect the presence of one or more phases of a seizure or to detect a transition time between phases of a seizure.

In some embodiments, a signal may be processed using a Morlet wavelet transform, Haar wavelet transform, Daubechies wavelet transform, harmonic wavelet transform or other suitable wavelet transform. Some wavelet transforms may provide for a more accurate reconstruction of input data than other transforms. However, generally, those wavelet transforms may demand somewhat greater processing resources than use of other wavelet transforms. Selection of one or more wavelet techniques may, in some embodiments, be based on those considerations and/or other considerations as described herein, including, for example, whether a method may be applied in real-time detection of seizures or may be applied in post-detection processing of stored or historical EMG signal data. And, in some embodiments, one or more Fourier or other frequency transforms may be substituted for the wavelet processing described herein.

In some embodiments, a wavelet transform signal data may be represented mathematically by a group of functions based on one or more mother wavelets. Generally, a mother wavelet may be represented schematically as shown in Equation 1.

$$\int \psi(t)dt = 0 \text{ [Limits } +\infty/-\infty\text{]} \quad \text{Equation 1}$$

A group of functions may then be generated from a mother wavelet by applying different scaling factors, which may, for example, be used to compress or stretch the mother wavelet. Other factors may be used to translate functions over time. For example, as shown schematically in Equation 2, a group or family of functions may be created from a mother wavelet using the factors a and b.

$$\Psi a,b(t) = 1/[a1/2]\psi[(t-b)/a] \quad \text{Equation 2}$$

By varying the factors (a) and (b), a series of functions may be created as suitable to focus on different frequency components of an EMG signal or EMG signal data.

Suitable systems which may, for example, be used for collecting large amounts of EMG and other patient-related data, organizing such data for system optimization or for execution of database queries, and initiating an alarm or other response based on suspected seizure activity are described in various ones of the references incorporated herein. For example, Applicant's U.S. application Ser. No. 14/920,665 includes a more detailed description of apparatus components which may be used in some of the embodiments herein. Systems may, for example, include one or more detection units, base stations, and other components. A detection unit may comprise one or more EMG electrodes capable of detecting electrical signals from muscles at or near the skin surface of a patient and delivering those electrical EMG signals to a processor for processing. The EMG electrodes may be coupled or attached to a patient and may, in some embodiments, be implanted within the tissue of a patient near a muscle that may be activated during a seizure. A processor suitable to process electrical EMG signals derived from EMG electrodes may be included in a detection unit or may be located elsewhere. For example, in some embodiments, a detection unit may send signals to one or more base stations. A base station may comprise a computer capable of receiving and processing EMG signals from a detection unit and/or data from other sensors, and may be used to determine from the processed signals whether a seizure may have occurred, and sending an alert to a caregiver.

FIG. 1 illustrates some embodiments of a method 10 for analysis of patient medical data collected using one or more sensors, including, for example, one or more sensors which may comprise or consist of EMG sensors. In some embodiments, method 10 may, as shown in step 12, include receiving EMG signal data. In some embodiments, EMG signal data may be received by accessing stored EMG signal data included in one or more databases, such as a medical database. As shown in step 14, one or more portions of EMG signal data may then be selected and/or removed from other portions of EMG signal data. For example, portions of EMG signal data collected during times near or including one or more seizure or seizure-related events may be removed from other portions of EMG signal data. Additional steps of the method 10 may then include processing the selected data in order to characterize seizure or seizure-related event data.

In some embodiments, receiving EMG signal data may include accessing EMG signal data stored in one or more medical databases, wherein portions of the stored EMG signal data may be sorted in order to identify or mark parts of EMG signal data associated with one or more seizure-related events or seizure-related events of one or more types. For example, in some embodiments, various types of seizure-related events may be marked, including, by way of nonlimited example, non-seizure movement events, seizure events, or both.

In some embodiments, marking of data may be accomplished by one or more caregivers. In some embodiments, a patient, a caregiver, and/or some other qualified person may mark data. For example, in some embodiments, a patient, a local caregiver and/or an associate of the patient may designate whether an event that triggered an alarm on a personal mobile detection device was an event of a certain type. For example, a patient or other nearby person(s) may be able to press one or more buttons on a mobile or personal mobile detection device in order to identify that an event that triggered an alarm was a false positive event (e.g., non-seizure movement event). Or, a patient (or other person(s) such as a local caregiver or family member of a patient, or other person) may be able to designate that an event that triggered an alarm was from an actual seizure. For example, a patient aware that they had just had a seizure or local caregiver may be able to mark on a computer or base station that an event that triggered an alarm was in fact from a seizure. For example, in some embodiments, a base station may automatically provide an input box suitable to add that information whenever an alarm is initiated. Other descriptive information about the seizure or care provided during a seizure episode may also be logged. Data related to markings of data may then, for example, be uploaded to a medical database along with other EMG signal data and received in the step 12 of method 10 together with EMG signal data. Or, data markings may be associated with EMG signal data in some other suitable way. Thus, data received in step 12 may include one or more markings identifying when one or more seizure-related events may be present (e.g., such as by time stamping event data on a base station or "dragging" a graphical window or bar across a graphical user interface) and other information about a seizure-related event, such as its type. Where EMG signal data included in a database is marked in order to identify where seizure-related events may be found in stored data (e.g., where time-stamped seizure-related events are marked) or where information indicating a seizure-related event type is included in a database, the EMG signal data may be referred to as marked or sorted EMG signal data. Accordingly, in some embodiments, methods and systems herein may be configured to enable any of a number of different person(s) to mark seizure-related event data, including, for example, a physician, a patient, a local caregiver, and combinations thereof.

In some embodiments, marked seizure-related event data and/or data collected adjacent or near seizure-related event data may be identified, selected and/or removed from other data in the step 14. For example, data markings may be included as searchable meta-data included along with other EMG signal data in a medical database. Meta-data may, for example, be added to a database along with EMG signal data when data is transmitted to a storage medical database from a base station.

In some embodiments, EMG signal data may be raw EMG data, EMG signal data collected in real-time, or EMG data in some other form, such as without prior detection or marking of seizure or seizure-related events. However, some embodiments of method 10 may be configured to analyze raw EMG signal data or other EMG signal data in order to detect seizure-related events that may not have been previously identified or marked. For example, as described in step 14, EMG signal data may be processed using one or more seizure-detection routines configured to detect one or more seizure-related events and select or remove one or more portions of EMG signal data including the one or more seizure-related events.

In some embodiments, EMG signal data selected in step 14 may be transmitted from one medical database to one or more processors having instructions for executing one or more additional steps included in the method 10. However, in some embodiments, a computer processor may include one or more medical databases and may also include one or more installed programs suitable for execution of the method 10, fully or in part. In some embodiments, a personal or mobile detection unit may include a computer processor configured to execute method 10, fully or in part.

In some embodiments, EMG signal data received in step 12 may be designated EMG seizure data. For example, in some embodiments, a trained epileptologist or other caregiver may use method 10 to analyze EMG signal data in order to assist in making a diagnosis or verifying a suspected diagnosis that one or more patients has epilepsy or some related condition. Accordingly, they may select to analyze designated EMG seizure data collected while a patient was expected to have had a GTC seizure or expected to have had a PNES event. Or, the caregiver may select to analyze designated EMG seizure data collected while a patient was expected to have had a seizure, but where the caregiver is unsure of whether the seizure should properly be classified as a GTC seizure or PNES event. For example, even after viewing video or other data, they may be unsure of whether the patient had experienced a seizure of a certain type. A caregiver may, for example, import EMG signal data or designated EMG seizure data into one or more computers suitably programmed to execute method 10. For example, programs configured to execute method 10 may be installed on one or more local computers operated or maintained by the caregiver. Alternatively, a caregiver may send designated EMG seizure data to one or more specialized operators trained to execute method 10 using one or more computers with a suitably installed program. In some embodiments, designated EMG seizure data may be marked so that one or more designated EMG seizure events may be readily selected from among other EMG signal data. Alternatively, a caregiver may only input one or more designated EMG seizure events and no substantive selection step may be needed to further analyze appropriate data, such as one or more designated EMG seizure events.

In some embodiments, EMG signal data received in the step 12 may include one or more seizure-related events sorted so that selected data may include or exclusively include either GTC seizures, PNES events, or a combination of both seizure-related event types. Some of those embodiments may be particularly well suited for making or verifying a diagnosis that a patient is experiencing one or more conditions, including, for example, epilepsy and/or a condition other than epilepsy, such as one that may include seizure or seizure-like manifestations.

In some embodiments, receiving of EMG signal data in step 12 may include collection of an EMG signal using one or more EMG electrodes disposed in association with one or more muscles of a patient. For example, method 10 may operate to characterize collected data and issue responses in real time. Method 130, described herein in relation to FIG.

10, provides additional details for some embodiments where received EMG signal data is provided in real-time. In this disclosure, unless the context clearly indicates otherwise, the description provided in method 130 may be used to support some embodiments of method 10. Likewise, unless the context clearly indicates otherwise, the description provided in method 10 may be used to support some embodiments of method 130. For example, appropriate limitations described with respect to either of the methods 10, 130 may be used in the other method.

In some embodiments, in step 14, selection of one or more portions of EMG signal data may include detecting, at least at some level of probability, one or more seizure events or one or more other events indicating increased risk of seizure occurrence. For example, one or more seizure-related events may be detected. Following detection of one or more seizure-related events, one or more parts of EMG signal data may be selected. For example, the selected data parts may include data collected during times near or including one or more of the detected seizure-related events. In some embodiments, selected data may have been collected at times preceding a detected seizure-related event, times including a detected seizure-related event, times following a detected seizure-related event, or any combination thereof. For example, selected reference data useful for normalizing EMG signal data, as described herein in relation to step 16, may have been collected at times preceding or immediately preceding a time or time range when a detected seizure-related event was physiologically manifested.

In some embodiments, detection of a seizure-related event may indicate a high confidence that a true seizure (e.g., a generalized tonic-clonic seizure or other seizure type commonly associated with epilepsy and/or the seizure disorder) may be occurring or may have occurred. However, in some embodiments described herein, selection of EMG signal data in step 14 may include detection of one or more seizure-related events which, while showing signs of being associated with a true seizure, may or may not indicate the presence of a true seizure or that a seizure was detected at high confidence. For example, in some embodiments, selection of data in step 14 may include detection of one or more signal amplitudes or detection of a rate of change of signal amplitude that may be elevated above some suitable threshold level. Those amplitudes and/or rates of signal amplitude change may indicate an increased risk of seizure occurrence, but those conditions may be insufficient to fully discriminate signals from some non-seizure sources which may also produce elevated EMG signal data. In some embodiments, further processing in additional steps beyond step 14 may be used to classify a detected seizure-related event and increase confidence that selected data may likely be associated with a true seizure. Alternatively, further processing in additional steps beyond step 14 may sometimes be used to identify that a detected seizure-related event may properly be categorized as a non-seizure movement or other seizure-related event type other than those of a true seizure. Thus, in some embodiments, processing of collected EMG signal using the method 10 may reduce the probability of false positive seizure detection.

In some embodiments, selection of data in step 14 may act as a trigger or filter for further processing. For example, further processing (e.g., processing in additional steps of method 14) of only selected EMG signal data may be useful to prevent resources, including human, battery, and/or computational resources, being unnecessarily allocated on indiscriminate data analysis. For example, in some embodiments where method 10 is executed as part of a patient monitoring strategy for real-time detection of seizure-related events, conservation of computational resources and/or battery resources may be extremely beneficial because it may, for example, extend useful battery life. In addition, in some embodiments, non-selective analysis and characterization of all signals, the majority of which may generally be non-seizure signals (such as when non-presorted EMG signal data is received in step 12), may not be desirable for other reasons. For example, indiscriminate processing and characterization of all collected EMG signal data (e.g., without any selection or data filter) may increase the chance that one or more spurious or false characterization results may be obtained. Accordingly, selection of data in the step 14 may act as a screen wherein, for example, only significant EMG signal data (e.g., EMG signal data known to be elevated in signal amplitude) may be characterized. However, various embodiments of method 10 may be executed wherein filters of different selectivity may be used. And, in some embodiments, EMG signal data may be processed without filtering or selection of data in the step 14.

In some embodiments, including, for example, those in which sorted, marked, or designated data was received or input in step 12, selection of data in step 14 may include identifying or organizing data in relation to one or more marked time points. For example, a caregiver sending EMG signal data for classification may already know approximately when a seizure-related event was physiologically manifested. Accordingly, relevant time points (e.g., time points marking the start of the event or pre-seizure-related event periods) may be marked and/or read into a processor executing the method 10. And, selection of data in step 14 may include reading the marked time points and identifying periods in relation to those time points.

Any of a number of suitable seizure-detection routines or combinations of seizure-detection routines may be used to detect seizure-related events and to select EMG signal data in step 14. For example, in some embodiments, any seizure-detection routine that may be used to detect a time or time range for suspected seizure activity, at least to some level of temporal resolution (e.g., high or low levels of resolution), may be applied in selection of EMG signal data. In some embodiments, one or more seizure-detection routines may be used to coarsely define a start time or time range for the start of a suspected seizure. And, as further described below, a more accurate determination of the start time of a seizure and/or other times associated with one or more phases of a seizure, may be determined in additional steps of the method 10.

In some embodiments, once a time or time range for the start of a seizure-related event may be determined, a portion of data that includes the start of the seizure-related event and/or one or more portions of data that include one or more other time periods may be selected and/or removed from other EMG signal data. For example, in some embodiments, if a seizure-related event is detected, then an approximately 10-minute portion of data, or data from some other suitable time period, may be selected and/or removed in step 14. For example, in some embodiments suitable for characterizing how a patient progresses during seizure recovery, even longer time periods of data may sometimes be selected. Data may be selected so that a start time or time range for a detected seizure-related event may be approximately centered or positioned in some other desired way within the selected data. Accordingly, in some embodiments, pre-seizure-related event periods of data may be identified within about the first half of the selected data. One or more pre-seizure-related event periods may then be divided out from the selected portion of data and used in further processing. For example, as described in step 16, in some embodiments, statistical informational calculated from the one or more pre-seizure-related event periods may be used to normalize or condition EMG signal data collected during a seizure-related event.

In some embodiments, any of a number of suitable seizure-detection routines or combination of seizure-detection routines may be applied in step 14 in order to detect seizure-related events. For example, in some embodiments, a seizure-detection routine may include analysis of EMG signal data collected over a time period and examination of the EMG signal data to look for one or more amplitude values that may exceed a threshold amplitude or exceed a threshold for a certain time period. In some embodiments, a seizure-detection routine may include examining EMG signal data collected over some time period and determining whether one or more data values among the EMG signal data may exceed one or more thresholds within one or more time windows within that period. And, based, for example, on a number of time windows or consecutive time windows in which the one or more thresholds were exceeded, a seizure-related event may be detected. In some embodiments, EMG signal data may be integrated, and one or more integrated data values may be compared to a threshold in order to detect a seizure-related event.

In some embodiments, data may be processed in other ways in order to facilitate detection of a seizure-related event in step 14. For example, in some embodiments, the magnitude of a statistical value related to levels of muscle activity and processed from signal isolated in one or more frequency bands may be determined. For example, in some embodiments, a statistical value may be a T-squared statistical value or principal component value that may not only be related to levels of muscle activity, but may also be more sensitive to seizure activity than other values related to muscle activity, including, for example, power content determined from one or more frequency bands. Methods of calculating T-squared statistical values and principal component values are described in greater detail in Applicant's U.S. Pat. Nos. 9,186,105, and 9,439,596, each of which is commonly owned by Applicant and fully incorporated herein by reference. In some embodiments, determination of a T-squared value may include processing of an EMG signal collected for a time period by filtering to select a plurality of frequency bands. For example, an EMG frequency spectrum may be broken up into a number of frequency bands, such as three or more, and one or more characteristics of each frequency band, such as an EMG signal amplitude or power content of the band, may be determined. A measured characteristic for a frequency band may be normalized by its variance and covariance with respect to the characteristic as measured in other frequency bands, and the resulting normalized values may be processed to determine a T-squared statistical value. Generally, unless the context clearly indicates otherwise, where reference herein is made to an amplitude of an EMG signal or EMG signal data, the magnitude of a statistical metric determined therefrom, including, for example, a T-squared value, principal component value, or other statistical value as described in the aforementioned references, may be used in some alternative embodiments.

In some embodiments, filtering or selection of EMG signal data in the step 14 may be used to modify a distribution of seizure-related event types. For example, all of the seizure-detection routines used herein to select data may generally act as filters to detect EMG data that may be related to seizures, such as GTC seizures. However, those routines may sometimes have different selectivities and/or sensitivities for detection of GTC seizures and/or PNES events. As used herein, the selectivity of detection for one or more types of seizure-related events refers to a proportion of seizure-related events of the one or more types that may be detected with respect to all detected seizure-related events when using a certain set of conditions. Sensitivity of detection for one or more types of seizure-related events is a metric that describes a proportion of all seizure-related events of the one or more types that are detected when using a certain set of conditions. Thus, as used herein, sensitivity of detection for one or more types of seizure-related events does not imply an ability to exclude other types of seizure-related events. For example, as noted above, some of the seizure-detection routines herein that include measurement of a T-squared statistical value or PCA value may be particularly sensitive in detection of seizure activity. Those routines may also have an acceptable level of selectivity for some embodiments of seizure event detection. Accordingly, those routines may be advantageously used in some embodiments where a personal mobile detection unit may be used to monitor a patient for detection in real-time, including some embodiments where the method 10 (and also method 130) is used for real-time monitoring of patients. Those routines may also be used in some embodiments where method 10 is applied as a post-process characterization/classification method.

In some embodiments, selection of EMG signal data in the step 14 may include execution of one or more seizure-detection routines configured to detect seizure-related event types, including, for example, GTC seizure types and PNES seizure types, with high selectivity. For example, some methods described in U.S. application Ser. No. 14/920,665, which is commonly owned by Applicant, may include detection of samples of EMG signal including elevated amplitude and may include techniques for qualification of samples which may be related to seizure activity. As further described therein, some embodiments for sample qualification may themselves be used to classify seizure-related events. In some embodiments herein, those routines may be used to select and prepare a dataset that may include either GTC seizures and/or PNES events. In some embodiments, additional steps in method 10 may then be used to differentiate GTC seizures from PNES events, thereby providing a specific method, suitable, for example, to diagnose the presence of PNES events.

For example, some embodiments where qualification of samples may be used to select EMG signal data may include detection of samples of electromyography signals including elevations in signal amplitude and qualification of the samples as including one or more properties to identify those samples as related to seizure activity. For example, in some embodiments, samples of an EMG signal may be qualified based on a comparison of criteria values to thresholds; wherein the criteria values include a duration width and one or more of a signal-to-noise ratio and an amplitude; and wherein the thresholds include a minimum duration width, a maximum duration width, and one or more of a minimum signal-to-noise ratio, minimum amplitude, and maximum amplitude. Some of those routines may be ideally suited for high selectivity detection of GTC seizure types and PNES seizure types.

In some embodiments, qualification of EMG signal data may also include grouping more than one sample together, with qualification accomplished by comparing an aggregate property of a group of samples to an aggregate property threshold. For example, included among aggregate qualification threshold values that may be used to qualify samples in a group are one or more of a minimum deviation value calculated from duration widths of samples or parts of samples, a maximum deviation value calculated from duration widths of samples or parts of samples, a minimum rate of sample repetition, a maximum rate of sample repetition, a minimum regularity of one or more sample characteristics, a maximum regularity of one or more sample characteristics, and/or combinations of the aggregate qualification threshold values thereof. However, in some embodiments suitable to select data for use in method 10, qualification may exclusively include qualification of individual samples. For example, qualification of individual samples may be suitable to select EMG signal data that may then be processed in additional steps of method 10 to classify and diagnose important medical conditions, such as PNES. Accordingly, methods herein may serve as an alternative mechanism for detecting PNES events that is different than other PNES detection methods, some of which may require more sensitive detection of individual samples and/or include more complicated methods of evaluating sample groups. For example, some embodiments of methods herein may, at least for some patients, provide an advantageous alternative to other PNES detection methods, such as those described in PCT/US16/28005, which is commonly owned by Applicant.

In some embodiments, as described in step 16, the one or more selected portions of EMG signal data may be normalized or conditioned based on one or more EMG signal data values calculated from EMG signal data collected during one or more pre-seizure-related event time periods. In some embodiments, normalizing or conditioning of the one or more selected portions of EMG signal data may include calculating an average or mean value of the amplitude of EMG signal data in one or more pre-seizure-related event time periods and subtracting the calculated value from EMG signal data collected during a seizure-related event. Alternatively, an appropriate statistical value related to a mean value, such as a median or mode value, may also be used. Thus, in some embodiments, EMG signal data for a seizure-related event may have any direct current (DC) offset signals substantially removed, thereby providing DC offset or corrected EMG signal data.

In some embodiments, normalizing or conditioning of the EMG signal data may include dividing DC offset or corrected EMG signal data (e.g., the data following the aforementioned subtraction) by a standard deviation or average standard deviation of EMG signal data collected in one or more pre-seizure periods. In some embodiments, an appropriate statistical metric associated with the spread of a dataset (e.g., spread, variance, average deviation, or other suitable statistical metric) may be substituted for a standard deviation.

In some embodiments, a plurality of pre-seizure-related event time periods may be selected in step 14, and one or more statistical values may be calculated from EMG signal data in each of the plurality of seizure-related event time periods in step 16. Where one or more statistical values of EMG signal data may be calculated in more than one pre-seizure-related event time period, pooled statistical metrics (e.g., a pooled mean or other pooled value) may be determined. In some embodiments, trends in statistical values over time may also be determined. For example, in some cases the magnitude of a mean value of the amplitude of EMG signal data and associated level of DC offset suitable for a patient may change near the start of a seizure. And, for example, an extrapolated statistical value may be used to estimate one or more DC offset corrections or other values used to normalize or condition data.

In some embodiments, normalizing and/or conditioning of EMG signal data may facilitate improved comparison of EMG signal data between patients and/or between monitoring sessions. For example, it may be useful to normalize EMG signal data by removing DC offset signals and/or adjusting EMG signal data based on pre-seizure noise levels so that data between patients or between monitoring sessions for a single patient may be more accurately characterized in automated and/or semi-automated analysis embodiments of method 10. In some embodiments, one or more measurements of the spread or noise in a pre-seizure-related event time period may serve as a first order estimate for properties of the skin/electrode interface as configured during times when a seizure-related event was detected. And, the aforementioned measurements may serve as a first order correction for differences in collection efficiency of electrical signals between different patients and/or between different monitoring sessions for one or more patients. Thus, some metrics characterized herein, including, for example, metrics related to seizure intensity, may be more accurately determined.

Figure 2A:
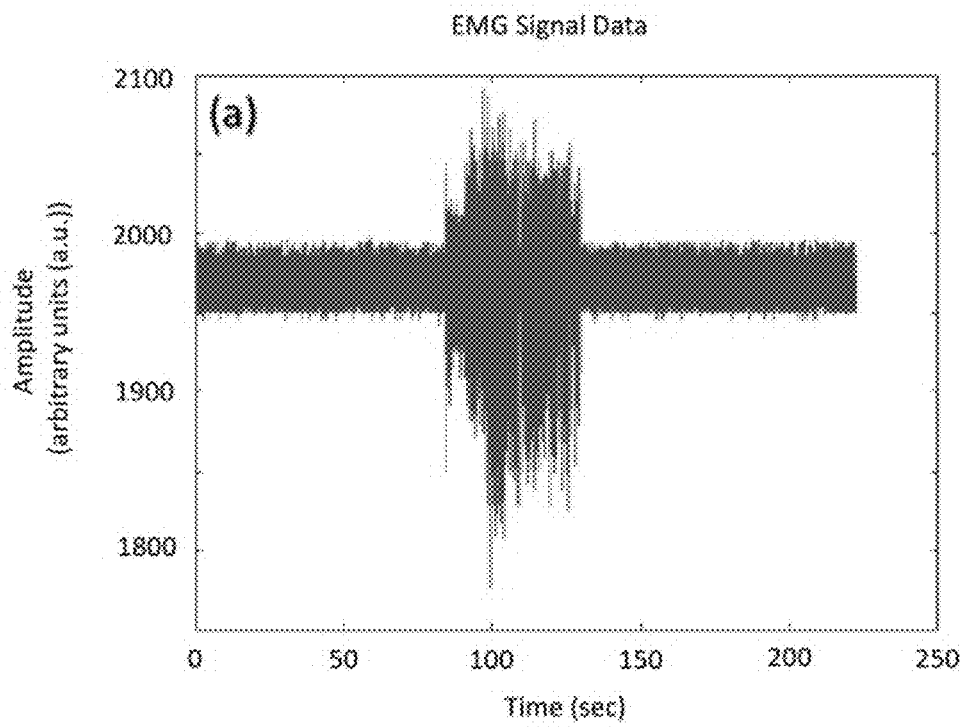
FIG. 2A shows EMG signal data for a patient.
Figure 2B:
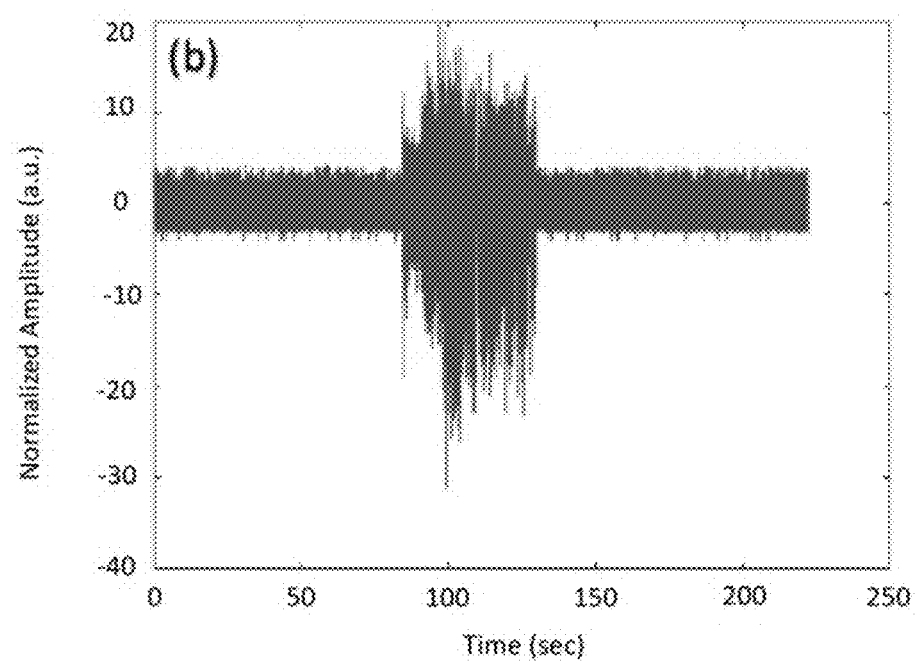
FIG. 2B shows conditioned EMG signal data derived from the EMG signal data of FIG. 2A.

By way of example, FIG. 2A shows EMG signal data collected from a patient having a generalized tonic-clonic seizure as is apparent between t=75 sec. and t=140 sec. FIG. 2B shows normalized EMG signal data following subtraction of a mean value calculated from a 100-second time period of pre seizure-related event data (not shown) from the data in FIG. 2A (i.e., wherein the signal data in FIG. 2A is the minuend and the mean value calculated from the 100-second pre-seizure data is the subtrahend) and division of the resulting difference by a standard deviation calculated from the same pre seizure-related event time period.

In step 18, EMG signal data may be processed using one or more frequency and/or wavelet transforms. Where EMG signal data is referred to in step 18 (and additional steps executed following step 18 in the method 10), unless the context clearly indicates otherwise, EMG signal data may refer to EMG signal data which may or may not be normalized or conditioned as described above in step 16. Where embodiments are specifically limited to normalized or conditioned EMG signal data, the term "conditioned EMG signal data" will be used. In some embodiments, EMG signal data may be processed with a Morlet wavelet, which may be used to express the complex power in frequency over time of EMG signal data. In such an approach, a Morlet wavelet may be used to transform EMG signal data into a form suitable for calculating magnitudes at which frequency components of the signal may be present at about a given time (e.g., within a certain temporal resolution) or over a given time interval. The Morlet wavelet transform may be characterized by Equation 3 and Equation 4. That is, the wavelet transform used may be:

$$C\left(a, b; f(t), \psi(t)\right) = \int_{-\infty}^{\infty} f(t) \frac{1}{\sqrt{a}} \psi\left(\frac{t-b}{a}\right) dt \quad \text{Equation 3}$$

where a is a scaling factor and b is a shifting factor (see also Equation 2). In Equation 3, f(t) is the signal analyzed and ψ(t) is the wave function. For example, in some embodiments, f(t) may include EMG signal data normalized or conditioned as described in step 16. In some embodiments, f(t) may include one or more portions of selected EMG signal data from step 14. Thus, in some embodiments, normalized or conditioned EMG signal data may be processed in step 18 or selected data in step 14 may be processed. In some embodiments, the wave function used may be:

$$\psi(sw) = \pi^{\frac{1}{4}} e^{-(s\omega-\omega_0)^2/2} U(s\omega) \qquad \text{Equation 4}$$

In Equation 4, $\omega_0$ is the center frequency, $s\omega$ is a scaled frequency and $U(s\omega)$ is the Heaviside step function.

Application of a wavelet transform on a signal may, for example, be used to produce a three-dimensional dataset wherein time and frequency components of the signal may sometimes be represented along the x and y axes, respectively, and an estimate of the signal magnitude may be indicated in a third dimension, such as may be indicated in a color coded or contoured plot.

In some embodiments, as shown in step 20, transformed EMG signal data may be organized in order to produce one or more groups of EMG signal data. Furthermore, in additional parts of step 20, one or more magnitudes of signals in the one or more groups of EMG signal data may be determined. For example, grouping of data may produce one or more groups of EMG signal data extending over one or more frequency ranges. And, the magnitude or amplitude of EMG signal data in the one or more frequency ranges may then be determined.

In some embodiments, organization of transformed EMG signal data and determination of one or more magnitudes of a group of EMG signal data may, for example, include integrating the transformed EMG signal data over one or more integration boundaries, binning the transformed EMG signal data, and generating a sum of data included in one or more created bins or collections of bins, or both.

A bin of EMG signal data may refer to a segment of EMG signal data bounded by a range of frequency and time. In some embodiments, integration or bin boundaries of transformed EMG signal data for frequency, time, or both may be scaled against a resolution limit of the transformed EMG signal data. For example, one or more of the aforementioned boundaries may be scaled in about a proportion to a frequency resolution limit, a temporal resolution limit, or both. In some embodiments, integration or bin boundaries may include a first boundary for one variable (e.g., time or frequency) that is held constant, and the other (or second) boundary (e.g., other of time or frequency) may be scaled against the resolution of the transformed EMG signal data for measurement of that variable.

In some embodiments, organizing data in the step 20 may include creation of a plurality of bins. For example, a plurality of bins may extend across all or some subset of a range of collected frequencies in an EMG signal. In some embodiments, a plurality of bins may be created wherein the plurality of bins may span one or more frequency ranges. For example, in some embodiments, about 190 bins (e.g., 193 bins) may be created. The bins may, for example, extend over a frequency range from about 3 Hz to about 420 Hz, or the bins may extend over some other frequency range described herein.

Figure 3:
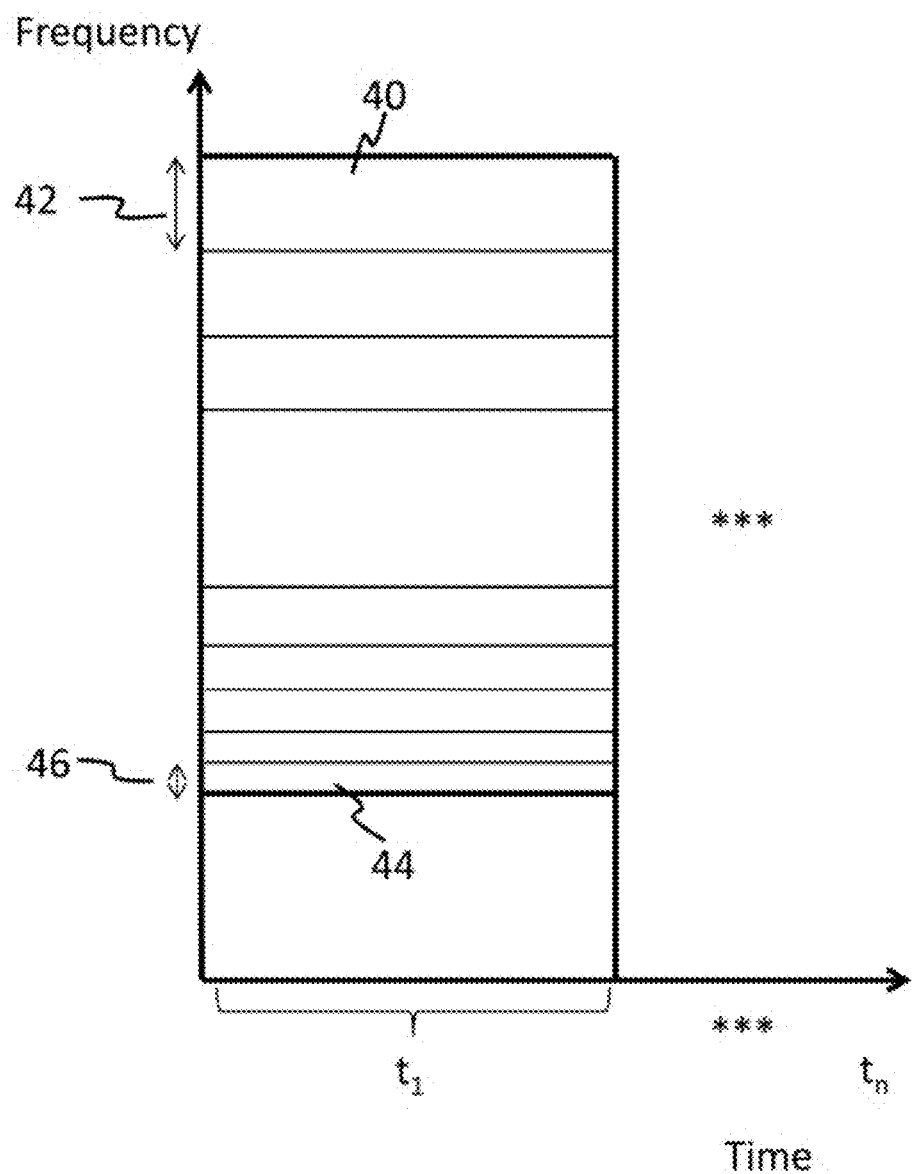
FIG. 3 is a schematic diagram showing some embodiments of bins.

As described above, in some embodiments, bins herein may include a frequency and/or time range boundary that is varied across either or both of frequency and/or time. For example, bin boundaries may be varied across either or both of a frequency and/or time range in proportion to how the resolution in frequency and/or time of the wavelet transformed signal data may change. For example, for any fixed interval of time, processing of EMG signal data with a wavelet transform may produce data with a frequency resolution that is greater in a low frequency range (where frequency resolution of the transformed signal may be higher) than in a high frequency range (where frequency resolution of the transformed signal may be lower). For example, as may be understood in reference to FIG. 3, a high frequency bin 40 may be configured to include data associated with the time interval (t1) and also associated with frequencies within a frequency range or interval 42. As also shown in FIG. 4, a lower frequency bin 44 may be configured to include data associated with the same time interval (t1) and also associated with frequencies within a frequency range or interval 46. The frequency range 46 associated with the bin 44 may include a narrower frequency range than the frequency range 42 associated with the bin 40. For example, the frequency ranges 42, 46 may be about proportional to a resolution limit for a signal included in each respective bin 40, 44. And, because the resolution limit in frequency is better at low frequencies, the range 46 is narrower than the range 42.

Still referring to step 20, in some embodiments, two or more collections of bins may be created from the transformed EMG signal data. For example, in some embodiments, a first collection of bins (or high frequency collection) may include one or more bins included in a frequency range from about 150 Hz to about 260 Hz. A group of EMG signal data including a high frequency collection of bins may be referred to as a high frequency group of EMG signal data. In some embodiments, a high frequency collection of bins may include one or more bins that may include a lower frequency boundary of about 120 Hz, about 150 Hz, or about 180 Hz. In some embodiments, the high frequency collection of bins may include one or more bins that may include an upper frequency boundary of about 200 Hz, about 260 Hz, about 300 Hz, or about 400 Hz. In some embodiments, all collected high frequency signals, which may be relatively weak above 400 Hz for most patients, may be included in a high frequency set of bins.

A second collection of bins (or low frequency collection) may include one or more bins included in a range of frequencies from about 6 Hz to about 70 Hz. In some embodiments, a low frequency collection of bins may include one or more bins that may include an upper frequency boundary of about 60 Hz, about 50 Hz, or about 45 Hz. In some embodiments, a low frequency collection of bins may include one or more bins that may include a lower frequency boundary of about 10 Hz, about 20 Hz, or about 30 Hz. A group of EMG signal data including a low frequency collection of bins may be referred to as a low frequency group of EMG signal data. In some embodiments including each of a high frequency and low frequency collection of bins, tonic and clonic phase seizure activity may be detected throughout the entire course of a generalized-tonic-clonic seizure. For example, two groups of EMG signal data may be used or used exclusively to perform seizure semiology. In some embodiments, groups organized in step 20 may include a first group of EMG signal data including or made from a collection of one or more bins extending across a high frequency band. And, a second group of EMG signal data may include or be made from a collection of one or more bins extending across a low frequency band.

In some embodiments, a first group of EMG signal data may include a high frequency collection of bins including one or more bins included in a range of frequencies above about 120 Hz. The high frequency collection of bins may sometimes include a high-frequency upper cut-off of about 400 Hz. More than one low frequency collection of bins may also be organized. For example, a first low frequency collection of bins may include one or more bins included in a range of frequencies from about 6 Hz to about 70 Hz. The lower frequency boundary of that first low frequency collection of bins may be about 10 Hz, about 20 Hz, about 40 Hz, or about 50 Hz. In some embodiments, one or more additional lower frequency collections of bins may be organized. For example, an additional low frequency collection of bins may include one or more bins included in a range of frequencies from about 2 Hz to about 10 Hz.

In some embodiments, in the step 20, one or more magnitudes of a high frequency group of EMG signal data and one or more magnitudes of a low frequency group of EMG signal data may be determined across one or more analysis time windows. In some embodiments, an analysis time window may, for example, extend across a time duration suitable to encompass pre-seizure time periods and the full duration of a typical GTC seizure or an expected duration for some other type of seizure-related event. In some embodiments, an analysis time window may extend across the full duration of EMG signal data selected in the step 14.

In some embodiments, one or more magnitudes of EMG signal data may be determined from one or more collections of bins. For example, in some embodiments, magnitudes of signal for at least one high frequency collection of bins and at least one low frequency collection of bins may be determined and tracked throughout all or some part of an analysis time window. For example, one or more bins may extend over a certain time increment or time unit in an analysis time window and also extend over one or more frequency ranges. In the step 20, bin magnitudes may be summed across each bin in a collection of bins. This process may be repeated across time (e.g., for other time increments or time units within an analysis time window) to derive magnitude data for one or more collections of bins across time.

In some embodiments, one or more magnitudes of groups of EMG signal data may be determined by integrating the transformed EMG signal data over boundaries with respect to frequency and/or time. For example, the transformed EMG signal data may be integrated over some increment or unit of time (e.g., an increment or unit of time within an overall analysis window) and over any of the aforementioned frequency ranges associated with any of various collections of bins as described above. The aforementioned integrations may be repeated for other time increments or time units within an overall analysis time window. Thus, an integrated magnitude or strength of signal in one or more bands may be tracked over any part of an analysis time window.

In some embodiments, a first group of EMG signal data may, for example, include data from a collection of one or more bins extending across a high frequency band, such as a band ranging from about 150 Hz to about 260 Hz. A high frequency collection of bins may further include data extending across some increment of time. For example, a collection of bins may extend over the aforementioned frequency range and some increment of time, such as an increment of time from about 10 milliseconds to about 100 milliseconds. For any given increment of time, a collection of bins may be analyzed. For example, a suitable metric related to the magnitude of signals in the collection of bins may be determined. For example, the magnitude of signals may be determined using one or more of a sum, mean, or median value for the bins in a collection. This analysis may be repeated for other increments over an analysis time window. Similarly, magnitudes for one or more other groups of EMG signal data, including, for example, groups extending across a low frequency band, may also be determined. That is, magnitudes of signals for bins extending over some frequency range and over an increment of time may be determined. The procedure may be continued for other increments extending across an analysis time window in order to produce EMG signal data across time. For example, such a procedure may produce magnitude data for one or more groups of EMG signal data as described below in FIGS. 4A and 4B.

In some embodiments, additional processing may also be performed in step 20. For example, in some embodiments, EMG signal data may be smoothed, one or more DC offset or baseline corrections may be applied, or both. For example, one or more envelope filters may be applied in order to smooth magnitude data for one or more groups of EMG signal data. As referred to herein, magnitude data for one or more groups of EMG signal data may refer to either magnitude data for smoothed EMG signal data or magnitude data for EMG signal data that has not been smoothed.

Figure 4A:
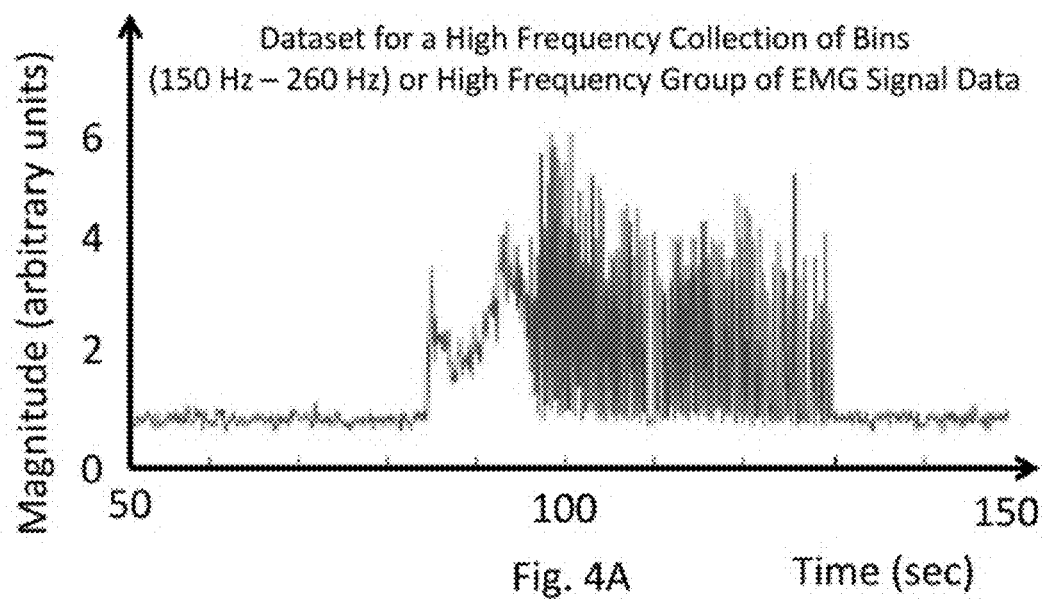
FIG. 4A shows magnitude EMG signal data for a group of EMG data including a collection of bins from a high frequency band.
Figure 4B:
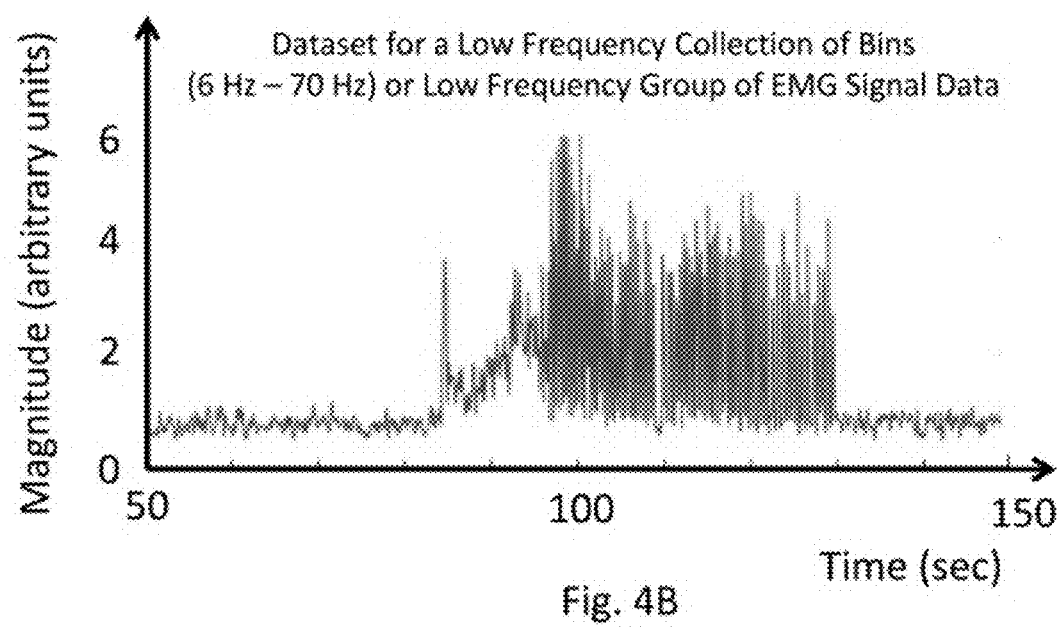
FIG. 4B shows magnitude EMG signal data for a group of EMG data including a collection of bins from a low frequency band.

For example, FIG. 4A shows magnitude data for EMG signal data for a collection of high frequency bins that extend over a range of frequencies of between about 150 Hz to about 260 Hz. FIG. 4B shows magnitude data for EMG signal data for a collection of low frequency bins that extends over a range of frequencies of between about 6 Hz to about 70 Hz. FIGS. 4A and 4B were derived without smoothing of data by passing EMG signal data through one or more envelope filters.

Figure 5:
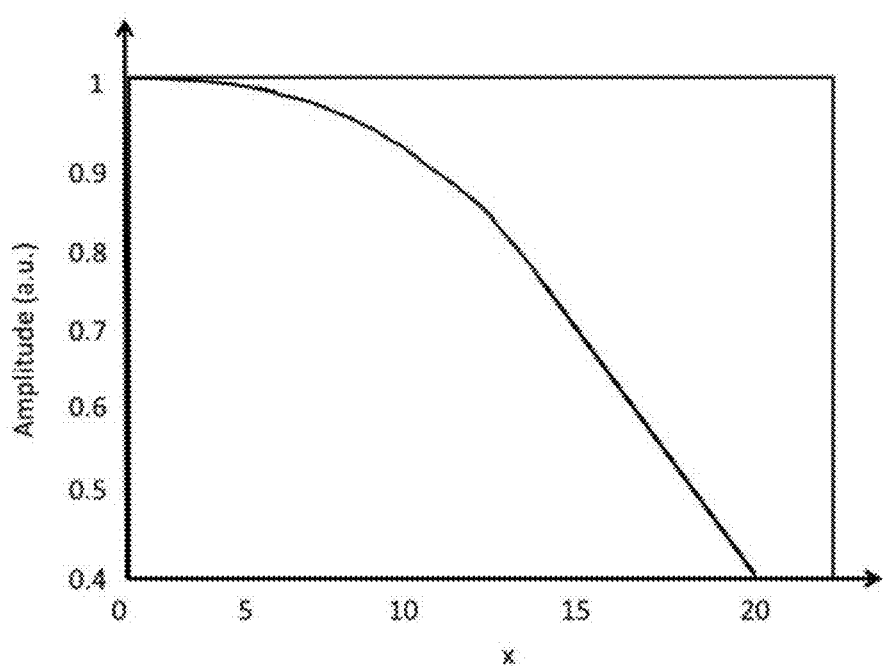
FIG. 5 shows data indicating the shape of an envelope filter.

As described above, in some embodiments, EMG signal data for one or more groups of EMG signal data may be processed using one or more envelope filters. For example, a representative envelope filter suitable for use in some embodiments herein is described by the exponential decay function shown in Equation 5 and further shown in FIG. 5.

$$f(x)=e^{-0.002x^2}, \text{ where } 0<x<20 \qquad \text{Equation 5}$$

Figure 6:
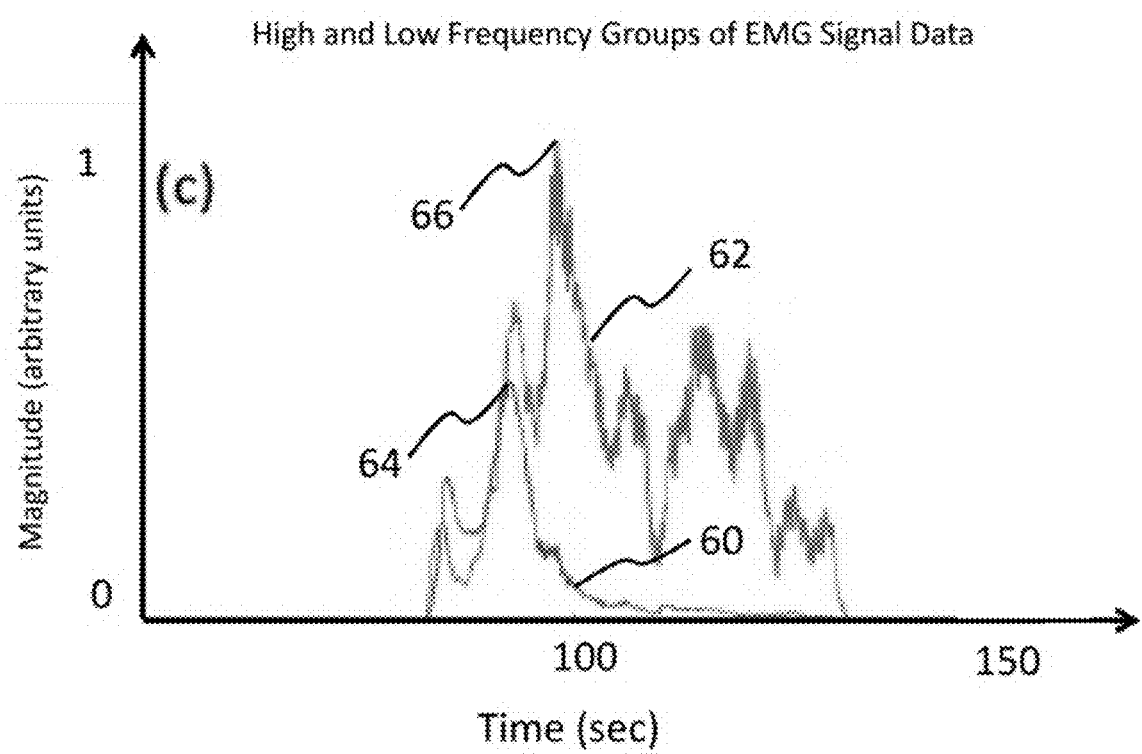
FIG. 6 shows magnitude data for EMG signal data for a high and low frequency group of signals.

FIG. 6 shows results obtained by processing the same datasets used in FIG. 4A and FIG. 4B with the exponential decay filter shown in Equation 5. In addition, the datasets shown in FIG. 6 have been baseline corrected to remove any DC offsets. In FIG. 6, the curve 60 indicates magnitude data for the high frequency collection of bins (about 150 Hz to about 260 Hz) and the curve 62 indicates magnitude values for the low frequency collection of bins (about 6 Hz to about 70 Hz). The data displayed in the curve 60 may be referred to as magnitude data for a high frequency group of EMG signal data, and the data displayed in the curve 62 may be referred to as magnitude data for a low frequency group of EMG signal data.

In some embodiments, as shown in the step 22, one or more magnitudes of one or more groups of EMG signal data may be scaled in order to produce one or more scaled magnitudes for the one or more groups of EMG signal data. For example, scaling of magnitude data may include dividing magnitude data for a group of EMG signal data by a maximum magnitude value achieved for the group of EMG signal data over an interval of time, such as a time interval within an analysis time window or within a part of an analysis window.

For example, referring to FIG. 6, a maximum magnitude or strength may be calculated for each of the high frequency and the low frequency datasets (e.g., curves 60 and 62, respectively in the example of FIG. 6). Specifically, for the dataset associated with the high frequency collection of bins, maximum magnitude 64 is shown. Similarly, for the dataset associated with the low frequency collection of bins, maximum magnitude 66 is shown. A maximum magnitude value may be an absolute maximum magnitude or a local maximum magnitude value. For example, in some methods where EMG signal data is evaluated in post-processing, collected EMG signal data for a duration or full duration of a detected seizure-related event may be available to a processor when determining scaled magnitude data. Accordingly, an absolute maximum magnitude value may be readily assigned. However, in some embodiments suitable for real-time analysis, one or more local maximum magnitude values may be assigned and/or used to calculate scaled magnitude data. In some embodiments, methods herein may determine if a local maximum magnitude value meets requirements to be designated an absolute maximum magnitude value for EMG data collected during a seizure-related event. For example, if a local maximum magnitude is maintained for greater than about 5 seconds to about 10 seconds (i.e., no other adjacent or following value exceeds the local maximum magnitude value), then the local maximum magnitude may be designated as an absolute maximum magnitude value. In some embodiments, other information, such as the slope or shape of EMG signal data on either side of a local/absolute maximum magnitude value may also be used in determining if the magnitude value is designated as a local or absolute magnitude value.

Figure 7:
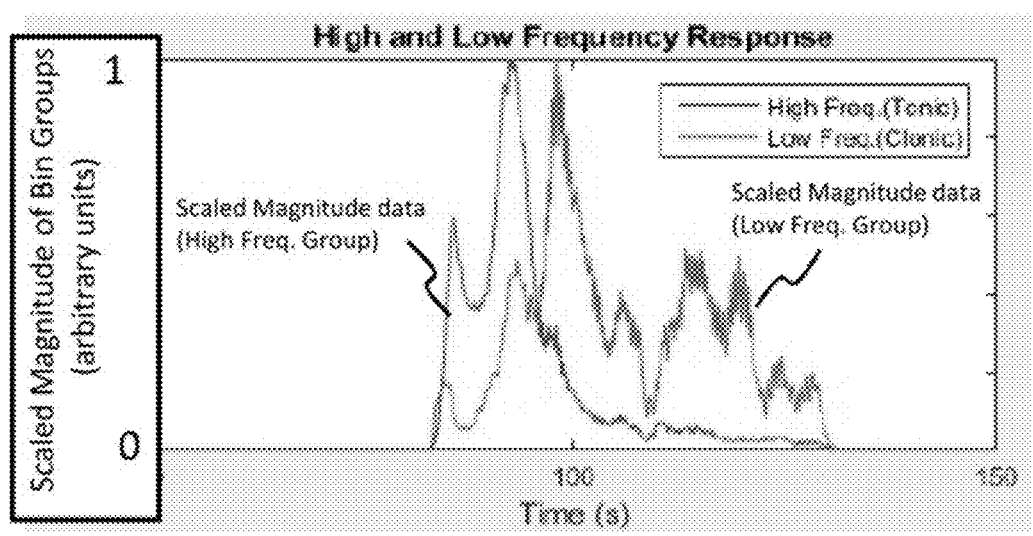
FIG. 7 shows scaled magnitude data for EMG signal data for the high and low frequency group of signals shown in FIG. 6.

Further by way of example, in order to scale magnitude data (step 22 of FIG. 1), a magnitude of data for the high frequency collection of bins (e.g., curve 60 in the FIG. 6) may be scaled by dividing the data by the maximum magnitude achieved within the high frequency dataset (e.g., magnitude 64 in the FIG. 6). The magnitude of data for a low frequency collection of bins (e.g., curve 62 in the FIG. 6) may be divided by a maximum magnitude achieved within the low frequency dataset (e.g., magnitude 66 in the FIG. 6). FIG. 7 shows the result of scaling magnitude data for each of the low frequency and high frequency signals shown in FIG. 6 based on respective maximum magnitudes for the two datasets.

As shown in the step 24 of FIG. 1, an analysis of magnitudes and/or scaled magnitudes may be executed in order to characterize seizure-related events. In some embodiments, characteristics of seizure-related events that may be determined in step 24 may include, by way of nonlimiting example, the duration of phases or parts of seizure-related events, event type, event intensity, and combinations thereof. In step 26, one or more responses may be initiated based, for example, on the identified characteristics of a seizure-related event. In some embodiments, step 24 and/or step 26 may include execution of one or more of the methods 90 and 110. For example, one or more of those methods (or one or more steps in those methods) may be executed as one or more sub-routines of method 10.

In some embodiments, analysis in step 24 may include comparison of one or more magnitudes or scaled magnitudes of one or more groups of EMG signal data to one or more thresholds. And, based on the comparison of magnitude and/or scaled magnitude data to one or more thresholds, one or more phases of seizure activity may be determined. For example, some of the embodiments herein may include detection of the presence of clonic-phase activity, tonic-phase activity, or both. Classification of seizure-related events may then include an evaluation of whether one or more of the aforementioned phases were detected. In some embodiments, transition times into and/or out of one or more phases of a seizure may also be determined.

Figure 8:
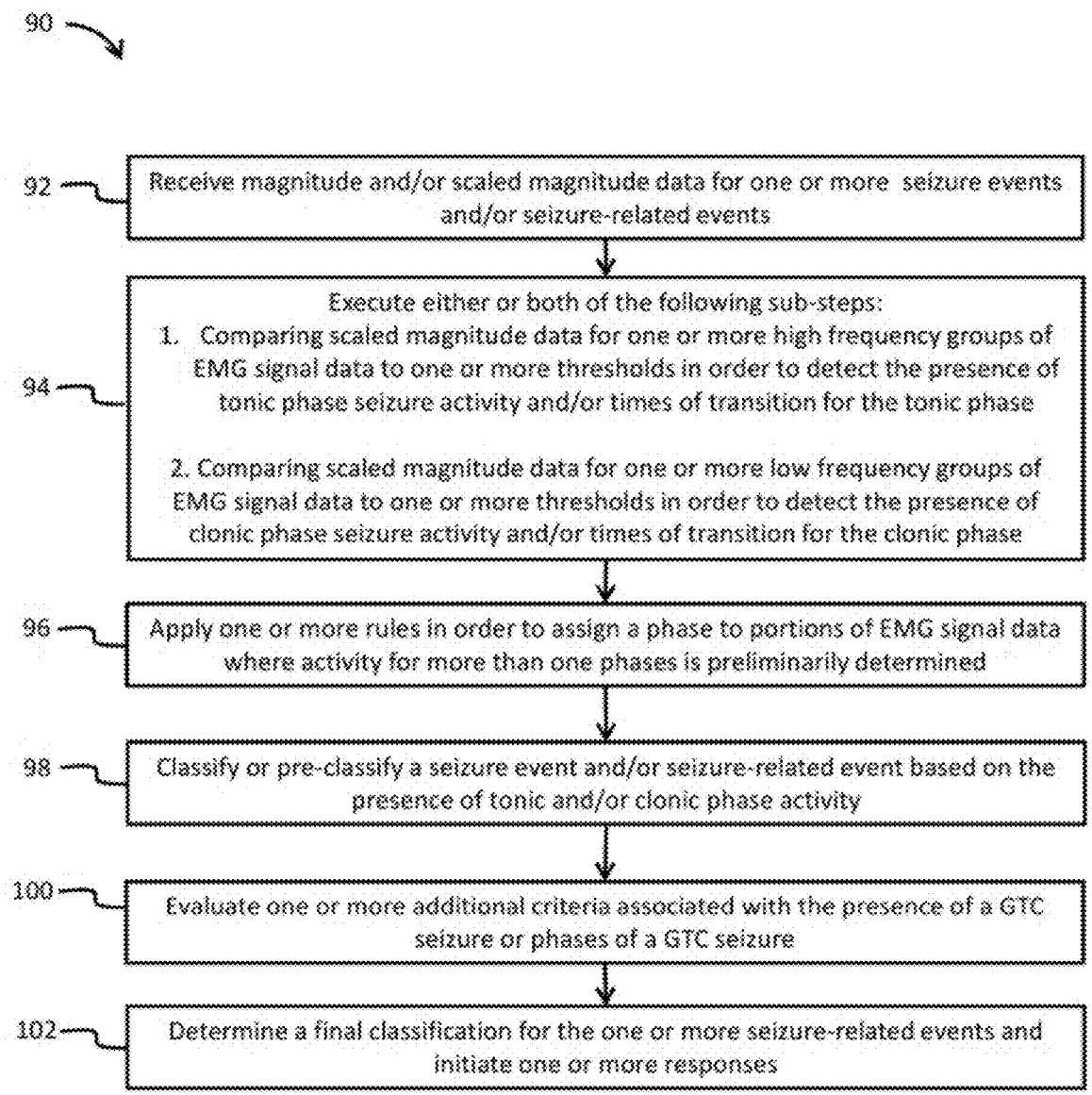
FIG. 8 is a flowchart showing some embodiments of a method or sub process for characterizing EMG signal data.

For example, in some embodiments, step 24 and/or step 26 of method 10 may include execution of the sub-routine described in method 90 (shown in FIG. 8). In the step 92, magnitude and/or scaled magnitude data for one or more detected seizure events and/or one or more seizure-related events may be received. For example, where method 90 is executed as a sub-routine in method 10, magnitude and/or scaled magnitude data may be determined as described above, (e.g., the data may include data for one or more high frequency groups of EMG signal data and one or more low frequency groups of EMG signal data). And, received seizure-related events may include one or more seizure-related events detected as described above, including in relation to step 14.

In some embodiments, as shown in step 94 (see sub-step 1), a scaled magnitude for one or more high frequency groups of EMG signal data may be compared to a threshold of about 0.65 to 0.90 in order to identify the tonic phase of a seizure. For example, in some embodiments, if a scaled magnitude of about 0.80 is determined for one or more groups of EMG signal data including a high frequency component of an EMG signal, a tonic phase may be recognized. In some embodiments, other thresholds within the above range may be used. For example, and without limitation, in some embodiments, within the above range of thresholds, thresholds of about 0.65, about 0.70, about 0.75, about 0.80, about 0.85, and about 0.90 may be applied.

In some embodiments, a transition time for the start of the tonic phase of a seizure may be identified based on detection of when a scaled magnitude for one or more high frequency groups of EMG signal data exceeds a threshold. For example, a transition time may be identified the first time a threshold is met, identified based on when some number of consecutive points meet the threshold, or identified based on some other suitable analysis of data points that may exceed a threshold. In some embodiments, transition out of a tonic phase may include determining when a scaled magnitude for one or more groups of EMG signal data including a high frequency component of an EMG signal fails to exceed a threshold. Alternatively, where a clonic phase follows the tonic phase, the duration of the tonic phase may be based on a determined time of transition into the clonic phase of a seizure, as described below.

In some embodiments, as shown in step 94 (see sub-step 2), a scaled magnitude for one or more low frequency groups of EMG signal data may be compared to a threshold of about 0.65 to 0.90 in order to identify the clonic phase of a seizure. For example, in some embodiments, if a scaled magnitude of about 0.80 is determined for one or more groups of EMG signal data including a low frequency component of an EMG signal, a clonic phase may be recognized. In some embodiments, other thresholds within the above range may be used. For example, and without limitation, in some embodiments, within the above range of thresholds, thresholds of about 0.65, about 0.70, about 0.75, about 0.80, about 0.85, and about 0.90 may be used.

In some embodiments, a transition time for the start of the clonic phase of a seizure may be identified based on detection of when a scaled magnitude for one or more low frequency groups of EMG signal data exceeds a threshold. For example, a transition time may be identified the first time a threshold is met, identified based on when some number of consecutive points meet the threshold, or identified based on some other suitable analysis of data points that may exceed a threshold. In some embodiments, transition out of a clonic phase may include determining when a scaled or unscaled magnitude for one or more groups of EMG signal data including a low frequency component of an EMG signal fails to exceed a threshold.

For some seizure events, during a certain time, such as transition between the phases, activity for each of the tonic and clonic phases of a seizure may be found to exceed one or more of the aforementioned thresholds. Accordingly, more than one phase of a seizure may be preliminarily identified. In some embodiments, as shown in step 96, methods herein may include determining if more than one phase are detected, and if more than one phase are detected, one or more rules may be applied in order to assign a phase. For example, in some embodiments, if both phases are preliminarily found to be active, the phase assigned may be based on one or more ratios between a group of EMG signal data including a high frequency component and a group of EMG signal data including a low frequency component. For example, in some embodiments, if both phases are found to be active, the phase may be described as tonic, unless the scaled strength of a group of EMG signal data including a low frequency component is found to be greater than about 1.25 times higher than the scaled strength of a group of EMG signal data including a high frequency component. For example, under that scenario, the seizure phase may then be classified as clonic. Alternatively, in some embodiments, no attempt may be made to classify times where both phases of activity are identified.

As shown in step 98, in some embodiments, a seizure-related event may be classified based on the presence of tonic and/or clonic phase activity. In some embodiments, if both clonic phase activity and tonic phase activity are detected, a seizure may be classified as a GTC seizure. In some embodiments, a seizure-related event may be classified as one including a clonic phase. For example, even if tonic phase activity fails to be detected, one or more responses may be initiated. For example, in some embodiments where the methods 10, 90 are used for real-time detection of seizure activity, one or more emergency or other alarms may be initiated based on detection of clonic phase activity. In some embodiments, a seizure-related event may be classified as one including a tonic phase. For example, even if clonic phase activity fails to be detected, one or more responses may be initiated. For example, at least for some patients or some patients under some conditions, exclusive detection of tonic phase activity may be used to identify seizure events that may not demand an emergency response.

In some embodiments, one or more additional routines may be executed in order to verify a classification made in step 98. Accordingly, a seizure-related event and/or seizure-event classified as above may, for example, be referred to as either a classified GTC seizure or pre-classified GTC seizure, based on whether additional classification steps are performed. In some embodiments, final classification of a seizure-related event that has been pre-classified as a GTC seizure (or other seizure type) may include analysis of one or more additional criteria. For example, in some embodiments, a first group of additional criteria, a second group of additional criteria, a third group of additional criteria, or any combination of the aforementioned additional criteria may be used to classify or verify the classification of a seizure-related event.

For example, as shown in step 100, in some embodiments, a first group of additional criteria may include whether magnitude data of one or more groups of EMG signal data meets one or more thresholds. For example, positive identification of a GTC seizure or a tonic-only event may include verification that magnitude data for one or more groups of EMG signal data including a high frequency component of an EMG signal meets or exceeds one or more magnitude thresholds. In some embodiments, the aforementioned magnitude data may be determined from data collected during times preliminarily classified to be part of a tonic phase portion of a seizure. For example, magnitude data may be selected from data included within what was preliminarily identified to be the tonic phase of a seizure. For example, a preliminary identification of the phase may be determined based on a comparison of scaled magnitude data from a high frequency group of EMG signal data to one or more thresholds as described above.

Similarly, a positive identification of a GTC seizure or a clonic-only event may include verification that magnitude data for one or more groups of EMG signal data including a high frequency component of an EMG signal meets one or more magnitude thresholds. In some embodiments, the aforementioned magnitude data may be determined from data collected during times preliminarily classified to be part of a clonic phase portion of a seizure. For example, magnitude data may be selected from data included within what was preliminarily identified to be the clonic phase of a seizure. For example, a preliminary identification of the phase may be determined based on a comparison of scaled magnitude data from a low frequency group of EMG signal data to one or more thresholds as described above.

In some embodiments, a first group of additional criteria may be deemed met if a magnitude value threshold is reached for data collected during what was preliminarily classified to be the tonic phase, if a magnitude value threshold is reached for data collected during what was preliminarily classified to be the clonic phase, or if both of the aforementioned conditions are met.

In some embodiments, a second group of additional criteria for classification of a GTC seizure (or other seizure-related event) may include whether one or more times for individual phase duration or total seizure duration meet one or more duration thresholds. For example, a second additional criteria for positive identification of a GTC seizure may include comparison of duration times for the tonic phase of a seizure, the clonic phase of a seizure, the entire seizure, or combinations thereof to one or more duration thresholds. For example, as described above, transition times into and out of one or more phases of a GTC seizure may be determined. Accordingly, duration times for phases of a GTC seizure may be readily determined by calculating the duration between appropriate transition times. And, in some embodiments, a second group of additional criteria for positive identification of a GTC seizure may include comparison of one or more duration times to one or more duration time thresholds (e.g., maximum duration time threshold, minimum duration time threshold, or both).

In some embodiments, a third additional criteria for positive identification of a GTC seizure may include determining whether a ratio between a magnitude of signals included in a high frequency group of EMG signal data and a magnitude of signals included in a low frequency group of EMG signal data meets one or more ratio thresholds. For example, in some embodiments, an integrated value for the area under a high frequency group of EMG signal data may be determined over the course of a seizure-related event or seizure-related event pre-classified to be a GTC seizure. For example, a seizure-related event may be expected to be a GTC seizure because it meets various criteria, including, for example, one or more of the criteria described above. Similarly, an integrated value for the area under a low frequency group of EMG signal data may be determined. Temporal boundaries for integration may be established from one or more transition times into and out of seizure phases (e.g., as may be determined based on comparison of scaled magnitude data to one or more thresholds). Alternatively, integration boundaries with respect to time may be selected in some other convenient way. For example, integration boundaries with respect to time may include some portion of EMG signal data selected in step 14, such as all selected data. In some embodiments, a ratio between magnitudes of high and low frequency groups of EMG signal data may be referred to as a qualified area under the curve ratio or QUAC ratio, which may be expressed as shown in Equation 6.

$$QUAC\,Ratio = \frac{\int_O^T HF(t)dt}{\int_O^T LF(t)dt} \quad \text{Equation 6}$$

In some embodiments, a QUAC ratio may be determined. If the QUAC ratio is greater than a lower QUAC ratio threshold, verification of the presence of a GTC seizure-related event may be confirmed. For example, a third additional criteria may be deemed satisfied. In some embodiments, a lower QUAC threshold ratio may be about 0.02 to about 0.04. In some embodiments, if the QUAC ratio is within each of a lower QUAC ratio threshold and a higher QUAC ratio threshold, verification of the presence of a GTC seizure-related event may be confirmed. For example, a third additional criteria may be deemed satisfied. In some embodiments, an upper QUAC ratio threshold may be about 0.5 to about 1.0. Of course, other suitable ratios may be defined in order to classify events. For example, in some embodiments, the denominator and numerator of the above QUAC ratio may be interchanged. Similarly, other appropriate ratio thresholds may be used.

As shown in the step 102, a final classification may be determined for any of the one or more seizure-related events analyzed. In some embodiments, the final classification may be the classification made in step 98. For example, no additional group of additional criteria may be evaluated. Alternatively, final classification may include evaluating whether one or more of the additional criteria described in relation to step 100 confirms or contradicts the presence of a pre-classified seizure-related event. For example, in some cases a pre-classified GTC seizure event may be deemed to be of an undetermined seizure-related event type if it fails to meet one or more of the additional group of criteria.

Further in step 102, one or more responses may be initiated. In some embodiments, a response may include organization of classification data and/or other characteristics data for a seizure-related event (e.g., duration times for detected phases) and providing the data to caregivers. For example, one or more reports may be generated.

In some embodiments, methods herein may include detection of when a patient may be experiencing a medical condition that resembles epilepsy, but where the patient may in fact be prone to experience PNES events. For example, in some embodiments useful for diagnosis or verification of a diagnosis that a patient may be suffering from PNES, designated EMG seizure data may be processed in order to classify designated EMG seizure events as either GTC seizures or PNES seizures. In some embodiments, EMG signal data including, for example, raw EMG signal data or sorted EMG signal data, may be analyzed. For example, EMG signal data including seizure-related events may be selected and classified in order to detect PNES seizures.

Figure 9:
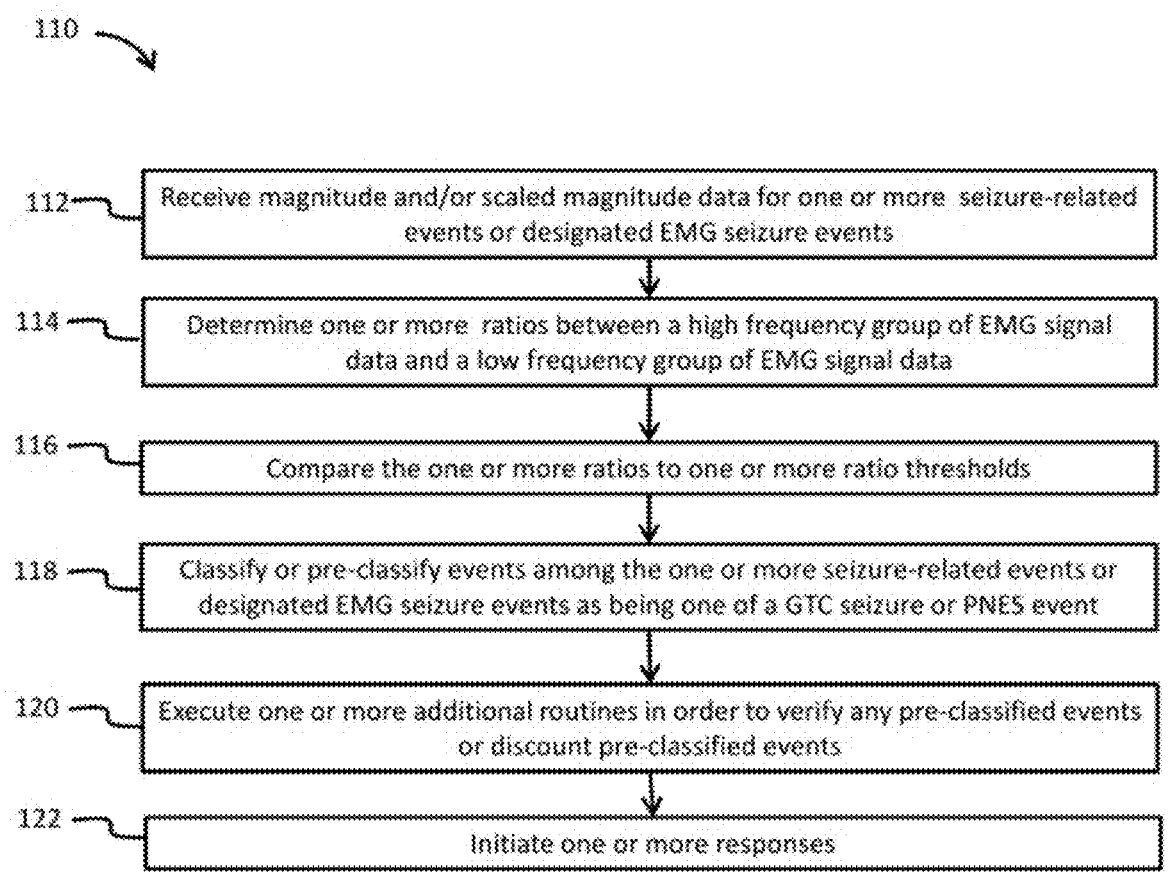
FIG. 9 is a flowchart showing some additional embodiments of a method or sub-process for characterizing EMG signal data.

For example, in some embodiments, EMG data may be evaluated using the method 10, wherein steps included in the sub-routine described in method 110 (shown in FIG. 9) may be included or used in execution of step 24 and/or step 26. For example, as shown in step 112, magnitude and/or scaled magnitude data for one or more detected seizure-related events or designated EMG seizure events may be received. Thus, in some embodiments, received magnitude and/or scaled magnitude data (step 112) may be derived from designated EMG seizure data. In other embodiments, received magnitude and/or scaled magnitude data (step 112) may be derived from EMG signal data that was selected in step 14 based on one or more seizure-detection routines. For example, in some embodiments, the one or more seizure-detection routines may be configured in order to achieve high selectivity for seizure events. For example, in some embodiments, the one or more seizure-detection routines may be configured in order to maintain high selectivity for detecting seizure events, even if such configuration may be achieved at the expense of detection sensitivity. For example, in some embodiments, the one or more seizure-detection routines applied in step 14 may be based on detection and qualification of samples of EMG signal including elevations, wherein thresholds for seizure detection are suitable for maintaining high selectivity. In some embodiments, received magnitude and/or scaled magnitude data (step 112) may be derived from sorted EMG signal data. For example, as described herein, sorted EMG signal data may be marked by one or more of a caregiver, patient, other persons, and combinations thereof in order to identify seizure events.

In some embodiments, as described in the step 114, one or more ratios between a high frequency group of EMG signal data and a low frequency group of EMG signal data may be determined. For example, one or more QUAC ratios may be calculated as shown in Equation 6. And, as shown in the step 116, the one or more QUAC ratios may be compared to one or more QUAC ratio thresholds. For example, it may be determined if a QUAC or other suitable ratio (such as an inverted ratio as described below) meets one or more threshold ratio conditions. In some embodiments, as described in step 118, one or more seizure-related events or designated EMG seizure events may be classified based, for example, on the comparison of QUAC ratios and thresholds. For example, in some embodiments, a QUAC ratio may be compared to an upper QUAC ratio threshold of about 0.02 to about 0.04. If the QUAC ratio is less than an upper QUAC ratio threshold, an event (e.g., seizure-related event or designated EMG seizure event) may be classified as a PNES seizure. In some embodiments, a QUAC ratio may be compared to one or more lower QUAC ratios, and if, for example, the QUAC ratio is greater than the lower QUAC ratio, an event may be classified as a GTC seizure. Of course, other suitable ratios may be defined in order to classify events as GTC and/or PNES events. For example, in some embodiments, the denominator and numerator of the QUAC ratio shown in Equation 6 may be inverted. Accordingly, other appropriate ratio thresholds may be used. For example, in some embodiments wherein the terms in the ratio in Equation 6 are switched, it may be suitable to determine if an inverted QUAC ratio is more than a lower ratio threshold in order to classify a seizure or seizure-related event as a PNES seizure.

Additionally, in some embodiments, as shown in step 120, one or more additional procedures may be initiated to verify a classification that an event should properly be characterized as determined based on the above comparison of one or more QUAC ratios to one or more thresholds. In some embodiments, where one or more additional procedures may be executed to verify a suspected classification, that classification may be referred to as pre-classification.

For example, in some embodiments, in the step 120, one or more steps in method 90 may be executed in order to increase confidence that a seizure classified as a GTC seizure according to method 110 is proper. Alternatively, if the additional procedures do not indicate that the pre-classification was correct, the pre-classification may be discounted or changed. In some embodiments, in the step 120, one or more steps may be executed to verify and/or discount a classification of one or more pre-classified events as PNES events. For example, in some embodiments, one or more routines may be executed to examine whether data suspected as being related to a PNES event is artificially periodic. For example, one or more of the routines further described, for example, in Applicant's U.S. Pat. No. 8,983,591 and associated with periodicity of signal data may be used to verify or discount one or more pre-classified events as being PNES events.

As shown in step 122, one or more responses may be initiated. For example, in some embodiments, classification data may be included in one or more reports which may be provided to a physician or other caregiver.

Figure 10:
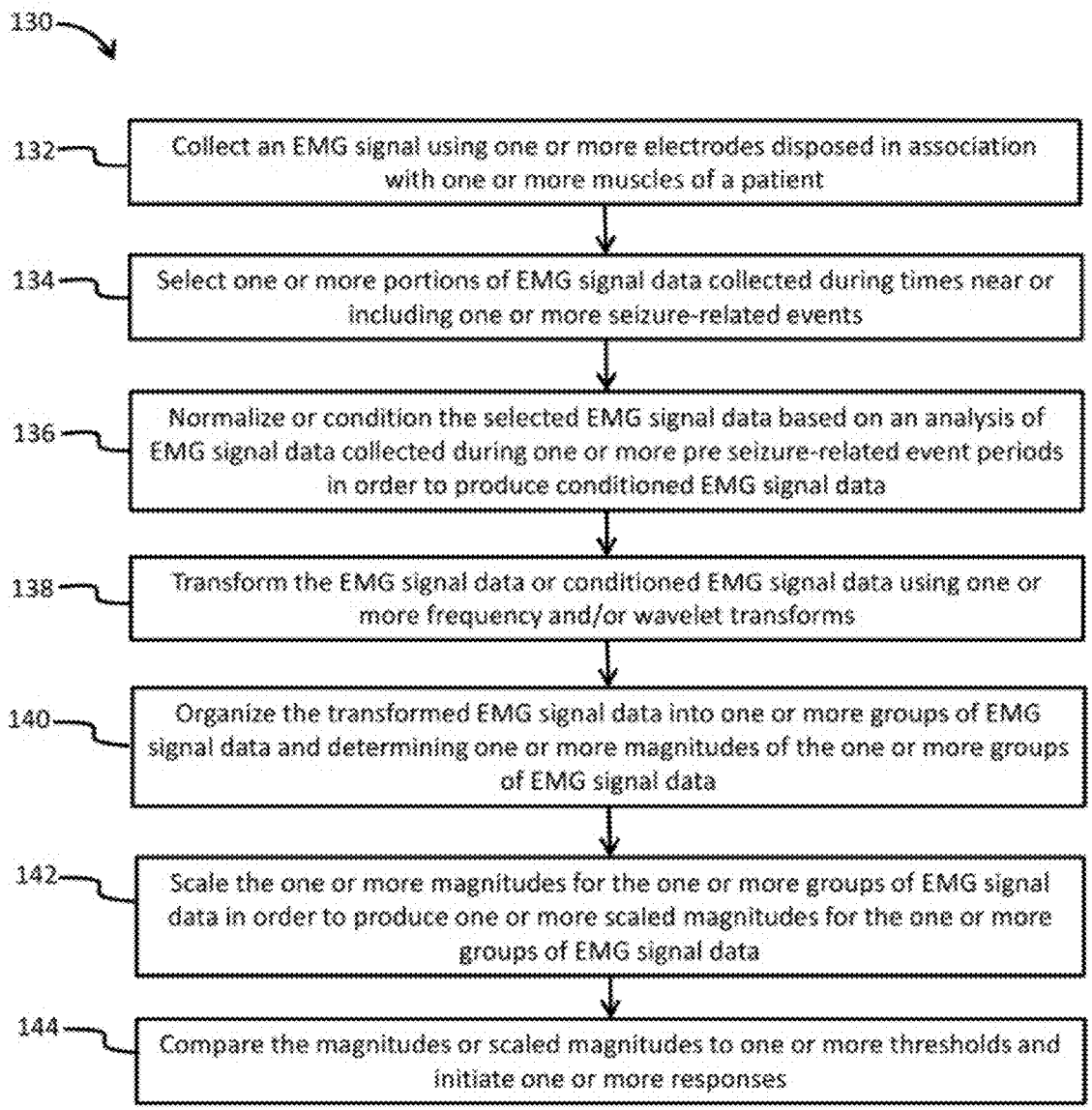
FIG. 10 is a flowchart showing some additional embodiments of a method for characterizing EMG signal data.

FIG. 10 illustrates some embodiments of a method 130 for analysis of patient medical data collected using one or more sensors, including, for example, sensors which may comprise or consist of EMG sensors. In some embodiments, method 130 may include analysis of collected medical data in real-time and may, for example, be used to initiate an alarm or other response suitable for a detected seizure, type of seizure, or seizure possessing certain characteristics.

As shown in step 132, collection of an EMG signal may include disposing one or more electrodes in association with one or more muscles of a patient. The electrodes may be suitably configured to transduce energy associated with muscle activation into a form that may be electronically processed. For example, in some embodiments, bipolar differential electrodes may be disposed on the skin of a patient near a patient's biceps, triceps, other patient muscle that may be activated during a seizure, and/or any combination of the muscles thereof.

In some embodiments, collected EMG signal may be processed to provide EMG signal data in a form suitable for input and/or processing in a computer processor. For example, in some embodiments, a collected EMG signal may be amplified and processed using an analog-to-digital converter in order to produce digital EMG signal data. In some embodiments, operations such as rectification, low pass filtering, and/or other operations that may be used to shape or condition an EMG signal may also be executed in the step 132.

In some embodiments, as shown in step 134, one or more portions of EMG signal data may be selected for further processing. For example, one or more seizure-detection routines may be used to detect one or more seizure-related events, and EMG signals near or including detected seizure-related events may be selected for further processing. In some embodiments, any suitable seizure-detection routine used for selection of EMG signal data as described in step 14 of the method 10 may be used in the step 134. In some embodiments, selection of EMG signal data in step 134 may include detecting a seizure-related event indicating the presence or increased risk of a seizure using one or more processors included in a detection device disposed on or near one or more of a patient's muscles. For example, one or more seizure-related events may be detected. In some embodiments, a detection device may be a device that is minimally intrusive to the patient and which may be configured to allow the patient to freely move during daily activity. In some embodiments, selected EMG signal data may be isolated from other EMG signal data and sent to a remote processor, such as may be included in a stationary base station, where the selected EMG signal data may be further processed in additional steps of method 130. However, in some embodiments, selected data in step 134 may be further processed within the same mobile detection device as used in selection of data in step 134.

In some embodiments, EMG signal data selected in step 134 may include data collected during, before, or after a detected seizure-related event. For example, as further described in step 138, selected data may be further processed using one or more frequency and/or wavelet transforms. In some embodiments, EMG signal data selected in step 134 and processing in step 138 may include a predetermined amount of EMG signal data collected adjacent or near a detected seizure-related event. For example, in some embodiments, all data collected over a 5-minute period (or some other suitable predetermined period) may be selected. Alternatively, EMG signal data selected for processing may include all data collected after detection of a seizure-related event in step 134. Or, all EMG signal data collected after detection of a seizure-related event but prior to a stop signal may be selected. For example, if EMG signal data collected after a detected seizure-related event returns to a baseline amplitude level, selection of data for processing may be stopped.

In some embodiments, step 134 may include execution of one or more seizure-detection routines that may run continuously or nearly continuously without drawing large amounts of energy from a battery or other source of energy. For example, as further described in U.S. Provisional Application 62/485,268, which is commonly owned by Applicant, seizure-detection routines that process relatively short segments of an EMG signal (e.g., less than about several seconds of data) in order to determine an amplitude value or some statistical values calculated therefrom, such as a T-squared statistical value or principal component value, may generally operate using limited computational resources and without drawing large amounts of energy from a battery or other source of energy, advantages which may be particularly beneficial when used with patient-worn or personal mobile detection devices where battery and computational or processing resources may be limited.

In some embodiments, a seizure-detection routine may compare one or more property values of an EMG signal to a threshold. For example, some seizure-detection routines may examine one or more short sections of an EMG signal data for the presence of an elevated EMG signal amplitude. If one or more elevated values of EMG signal amplitude are detected that are above one or more thresholds, a response may be almost immediately initiated. In some embodiments, seizure-detection routines executed in the step 134 may evaluate one or more segments of EMG signal data in order to determine an amplitude value or some statistical values calculated therefrom, such as a T-squared statistical value or principal component value. The aforementioned property values may be compared to one or more thresholds in order to determine if a seizure-related event is detected and to select EMG signal data in the step 134.

In some embodiments, one or more seizure-detection routines may be used to detect a time or time range for the start of seizure activity. Once a start time or time range for the start of a seizure is determined, a portion of data that includes the start of the seizure and/or a portion of data that includes one or more pre-seizure time periods may be selected. For example, if detection of a seizure-related event identifies that a seizure may have occurred sometime within about the last 60 seconds before an estimated start time of the seizure-related event (or other range consistent with the temporal resolution for detection of a seizure-related event), a pre-seizure-related event may be selected from data collected about 60 seconds or more before that estimated start time of the seizure-related event. Accordingly, one or more pre-seizure periods may be divided out and used in further processing. For example, statistical informational calculated from one or more pre-seizure periods may be used to normalize or condition EMG signal data, as described in the step 136.

In some embodiments, as shown in step 136, selected data may be normalized or conditioned. For example, normalization or conditioning of data may include steps as described in step 16 of method 10.

As shown in step 138, EMG signal data or conditioned EMG signal data may be processed using one or more frequency and/or wavelet transforms. In some embodiments, the one or more frequency and/or wavelet transforms may execute over some predetermined interval or until some stop signal is triggered to prevent further selection of data for processing. In some embodiments, a wavelet transform used in step 138 may be one suitable for application in real-time detection. For example, a Morlet Wavelet or other suitable wavelet may be used.

As shown in step 140, EMG signal may be organized in one or more groups, and magnitudes of signals in the one or more groups may be determined. For example, in some embodiments, data may be organized in one or more collections of bins. The collections may, for example, include one or more high frequency collections of bins and one or more low frequency collections of bins as described in detail in step 20 of the method 10.

As shown in step 142, magnitude data may be scaled. Scaling of magnitude data may include dividing magnitude data for a group of EMG signal data by a maximum magnitude value achieved for the group of EMG signal data over some time period. As further described in step 22 of the method 10, scaling of magnitude data may include determining one or more absolute maximum magnitude values or one or more local maximum magnitude values. For example, when scaling magnitude data collected over time, one or more local maximum magnitude values may be determined and used to scale data. And, in some embodiments, methods herein may determine if a local maximum magnitude value meets requirements to be designated as an absolute maximum magnitude value. For example, in some embodiments, if a local maximum magnitude is maintained for greater than about 5 seconds to about 10 seconds (e.g., no other adjacent or following values exceed the local maximum magnitude value), then the local maximum magnitude may be designated as an absolute maximum magnitude value. In some embodiments, other information, such as the slope or shape of EMG signal data on either side of a local/absolute maximum magnitude value may also be used in determining if a magnitude value is designated as a local or absolute magnitude value. In some embodiments, one or more responses initiated in step 144 may be made only if scaled magnitude values have been determined to be based on an absolute maximum magnitude value.

As shown in step 144, magnitudes or scaled magnitudes for one or more groups of EMG signals may be compared to one or more thresholds. Based on the comparison, one or more responses may be initiated.

In the method 130, determined magnitudes and scaled magnitude of EMG signal data (steps 140, 142) may be determined across time. For example, organization of EMG signal data in one or more groups of EMG signal data (step 140), calculation of magnitude data for the organized groups (step 140), and scaling of magnitude data (step 142) may be performed over one or more time intervals. The process may then be repeated for other intervals of time during an analysis. Continuously or periodically within this process, such as every 1 second or at other suitable time interval, magnitude and/or scaled magnitude data may be analyzed and one or more responses may be initiated. For example, in some embodiments, one or more alarms may be initiated if a seizure-related event is determined to be a GTC or other seizure event type based on one or more of the characterization steps described herein.

Figure 11:
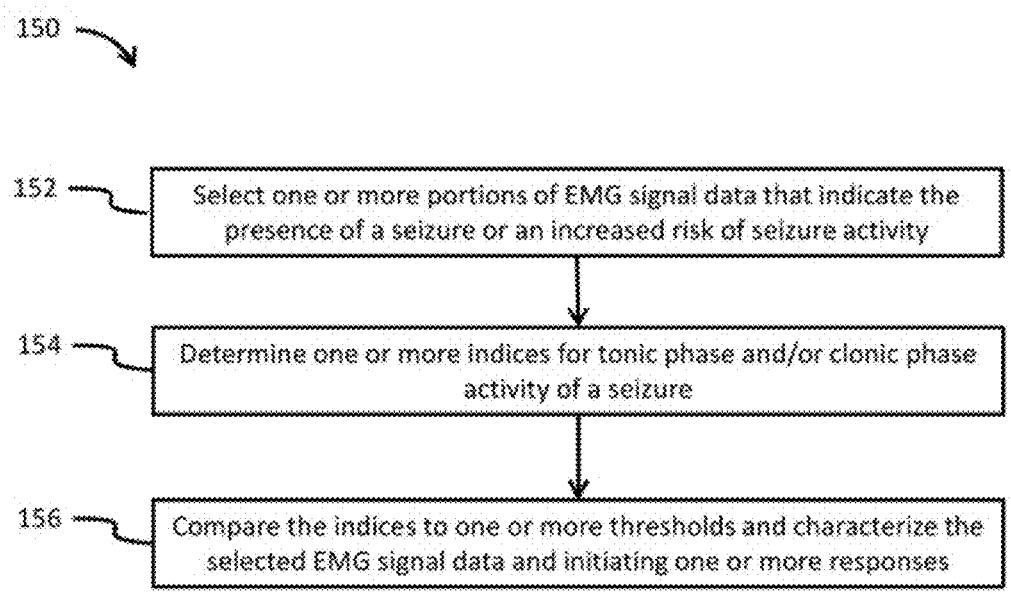
FIG. 11 is a flowchart showing additional embodiments of a method for characterizing EMG signal data.

FIG. 11 illustrates embodiments of a method 150 for processing EMG signal data. Method 150 may, for example, be run independently of method 10 or used in combination with the method 10. For example, indices for the tonic and clonic phases as described herein may be used help characterize whether a GTC seizure or other activity is present. The method 150 may be used to distinguish some detected events that may be indicative of non-seizure sources from true seizures. For example, some non-seizure events may be detected by some seizure-detection routines and may be characterized by the presence of high magnitude data that may be large but not sustained over time. Method 150 may be used to identify such activity and used to discriminate non-seizure events from true GTC seizures.

In a step 152, method 150 may include selection of one or more portions of EMG signal data. Selection of one or more portions of EMG signal data may include detecting, at least at some level of probability, one or more seizure events or one or more events indicating increased risk of seizure occurrence. Selection of data that may include a seizure is further described in greater detail in, for example, step 14 of the method 10. For example, in some embodiments, an about 10-minute portion of data may be selected and used for processing in the step 152.

In a step 154, one or more indices of tonic phase and/or clonic phase activity of a seizure may be calculated. For example, indices of seizure activity for the tonic and clonic phases of a seizure may be calculated as shown in Equation 7 and in Equation 8, respectively.

$$I_T = k1 \int (\text{Magnitude(High Freq.)}) dt \text{ where, } 0 < t < x \quad \text{Equation 7}$$

$$I_C = k2 \int (\text{Magnitude(Low Freq.)}) dt \text{ where, } 0 < t < x \quad \text{Equation 8}$$

In Equation 7, the tonic phase index ($I_T$) includes a scaling factor k1 and an integrated value across time for signal magnitude calculated for a high frequency group of EMG signal data. For example, magnitude data as described in step 20 of method 10 may be included in Equation 7. In other embodiments, scaled magnitude data (as may be determined in the step 22 of method 10) may be used. In Equation 8, the clonic phase index ($I_C$) includes a scaling factor k2 and an integrated value across time for signal magnitude calculated for a lower frequency group of EMG signal data. In other embodiments, scaled magnitude data (as may be determined in the step 22 of method 10) may be used. Operations and steps associated with determining of magnitude and/or scaled magnitude data (as used in Equations 7 and 8), such as, for example, wavelet processing and normalization, are described in greater detail in reference to method 10.

In a step 156, indices for the tonic and clonic phases may be used to characterize the selected EMG signal data. For example, in some embodiments, for a dataset to be characterized as a true GTC seizure, both the tonic and clonic indices may exceed a threshold value. In some embodiments, scaling factors k1 and k2 may be selected so that a threshold value of 1 may be used to indicate characterization of tonic and/or clonic phase activity. In some embodiments, indices for the tonic and clonic phases of seizures may be evaluated across time or during one or more analysis windows. For example, in Equations 7 and 8, magnitude values for the high and low frequency groups of EMG signal data may be evaluated over an interval of about 10 minutes. However, in some embodiments, indices for tonic and clonic activity may be evaluated continuously over time or at some number of discrete times. Accordingly, characterization of signals (step 156) may also be executed across time. For example, in some embodiments, indices may be evaluated at regular intervals following times identified when a seizure or possible seizure may have occurred. For example, at regular intervals following detection of seizure or possible seizure activity, such as at intervals of between about 30 seconds to about 240 seconds, indices for tonic and clonic phase activity may be evaluated. In some of those embodiments, scaling factors k1 and k2 may depend upon time (e.g., the scaling factors k1 and k2 may change during the progression of a suspected seizure) and may be described as k1(t) and k2(t).

Additional information related to the methods and apparatus described herein may be understood in connection with the examples provided below.

Example 1

In this Example 1, a patient susceptible to seizures was monitored for seizure activity using EMG electrodes. A sensor was placed on the patient's biceps, EMG signals were collected, the collected signals were analyzed for the presence of seizure activity, and a seizure was detected. The seizure was post-process characterized using a procedure including organization of two collections of bins in order to form a high frequency and a low frequency group of EMG signal data. For example, a high frequency collection of bins was organized which included bins extending over a range from about 150 Hz to about 260 Hz. A lower frequency collection of bins was organized which included bins extending over a range from about 6 Hz to about 70 Hz. Magnitudes and scaled magnitudes for the two bin collections were determined across time and compared to thresholds suitable to indicate if the tonic phase was present (based on the high frequency data from about 150 Hz to about 260 Hz) and/or if the clonic phase was present (based on the lower frequency data from about 6 Hz to about 70 Hz). A threshold for detection of activity was set to 0.8.

Figure 12:
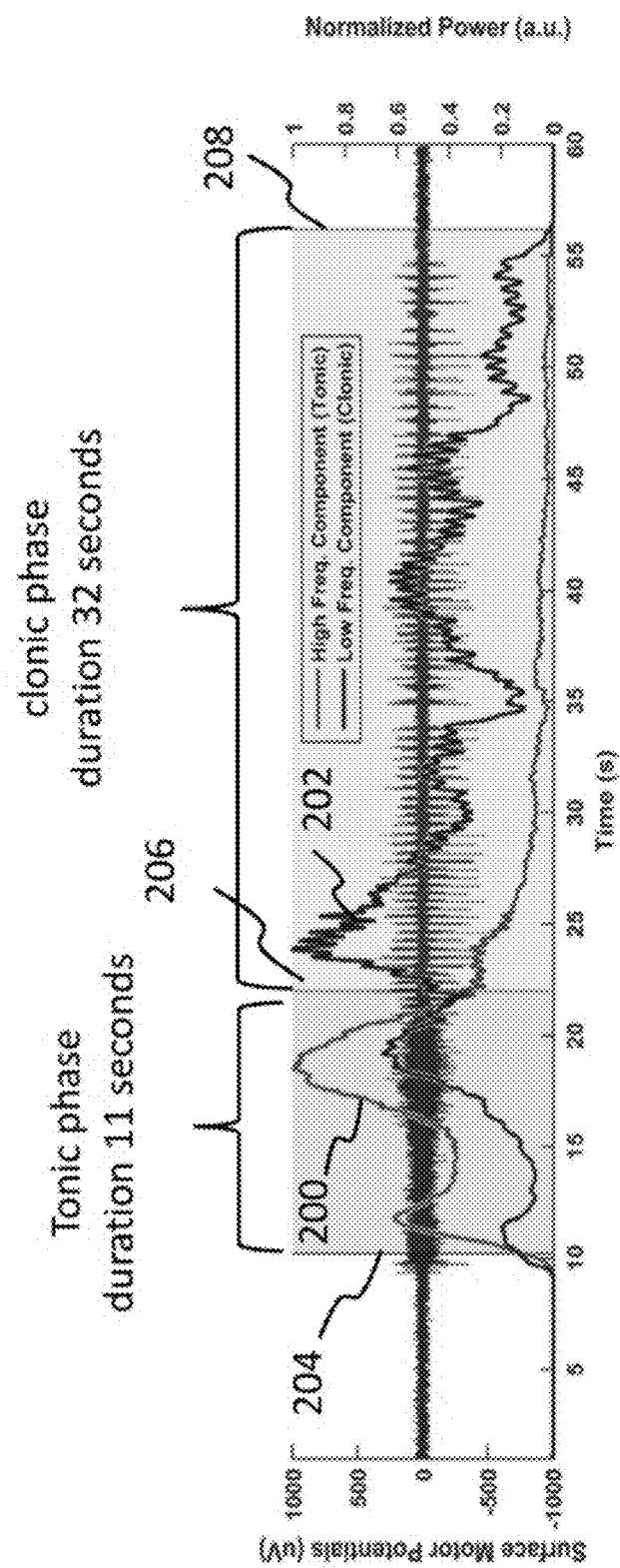
FIG. 12 shows EMG signal data and determined transition times for various phases of a GTC seizure.

Results for analysis of the detected seizure are shown in FIG. 12. In FIG. 12, amplitude of EMG signal data (surface motor potentials) is plotted against time. In addition, scaled magnitudes for the high frequency data (200) and low frequency data (202) used herein are shown superimposed on the EMG signal data. Determined times for transition into the tonic phase of the seizure (204), clonic phase of the seizure (206), and transition out of the seizure (208) are also shown therein. Specifically, the seizure detected herein had a tonic phase duration of about 11 seconds, a clonic phase duration of about 32.3 seconds, and a total seizure duration of about 43.3 seconds.

Example 2

In this Example 2, a patient was monitored for seizure activity using EMG electrodes. A sensor was placed on the patient's biceps, EMG signals were collected, and the collected signals were analyzed for the presence of increased EMG signal amplitude events that may be indicative of an increased risk of seizure activity. A number of such events indicating seizures and/or possible seizures were detected. For this patient, 6 events were identified of which 2 events were verified to be true GTC seizures. The events were post-process analyzed using the method 150. In this Example 2, a high frequency group of bins, which included bins that extended over a range of frequencies from about 150 Hz to about 260 Hz, was used for creation of a tonic index. A low frequency group of bins, which included bins that extended over a range of frequencies from about 6 Hz to about 70 Hz, was used for creation of a clonic index. The results of processing the 6 events in this Example 2 are shown in Table 1.

TABLE 1

| Detection Event | Tonic Index | Clonic Index | Characterization |
| --- | --- | --- | --- |
| 1 | 0.80732 | 0.62387 | Non-seizure |
| 2 | 2.5524 | 0.23664 | Non-seizure |
| 3 | 1.8692 | 3.6207 | GTC seizure |
| 4 | 0.6367 | 0.1389 | Non-seizure |
| 5 | 0.62234 | 0.13739 | Non-seizure |
| 6 | 1.8124 | 3.4045 | GTC seizure |

Example 3

In this Example 3, a multicenter trial was conducted to monitor patients for seizure activity. In the trial, both EMG signal data and EEG signal data were collected. Trained EEG technicians were asked to review the data for any suspected PNES events. Trained epileptologists were then asked to review any suspected PNES data in order to classify PNES events characterized by abnormal muscle movements. Specifically, three trained EEG epileptologists reviewed the EEG data, and seizure-related events were deemed to be PNES events was deemed if two out of the three epileptologists identified the event as a PNES event. Ten PNES events were classified based on this procedure.

EMG signal data collected for all events classified as PNES events was then tested against a T-squared seizure-detection routine. All of the classified PNES events identified using the EEG data were also detected when using the T-squared seizure-detection routine. In addition, ten randomly selected GTC seizure events from the multicenter trial were also analyzed and detected using the same T-squared seizure-detection routine. The detected events were then selected for processing using methods herein. In particular, the data was processed in order to determine magnitude data in each of a high frequency and a low frequency group of EMG signal data. In this Example 3, high frequency data was collected for a group of bins in a frequency band from about 150 Hz to about 260 Hz. Low frequency data was collected for a group of bins in a frequency band from about 6 Hz to about 70 Hz. QUAC ratios were then determined as described in Equation 6 and as further described in relation to method 110. For PNES events, boundaries for integration for QUAC calculations were selected to include the full duration of the events. For GTC events, two separate analyses were tested. In a first analysis, as described herein in reference to FIG. 13A, integration boundaries for QUAC calculations extended across the full length of the seizure events. In a second analysis, as described herein in reference to FIG. 13B, integration boundaries for QUAC calculations were selected in order to separately consider the tonic and clonic phases of each detected event. For example, end points for transitions into and out of the two phases may be determined from scaled magnitude data and comparison to thresholds as described in relation to method 10.

Figure 13A:
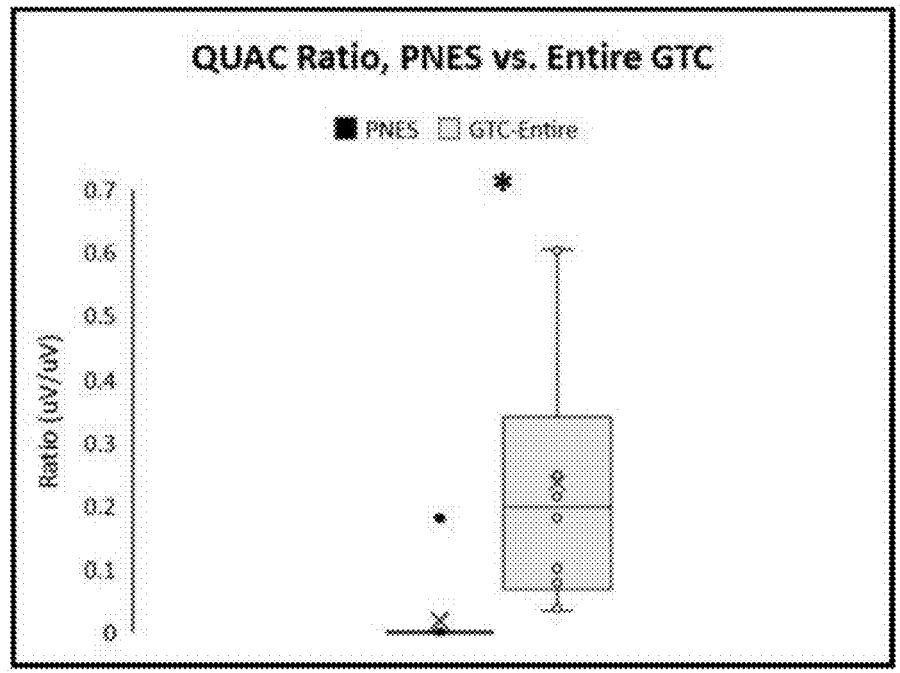
FIG. 13A shows QUAC data for GTC and PNES events.
Figure 13B:
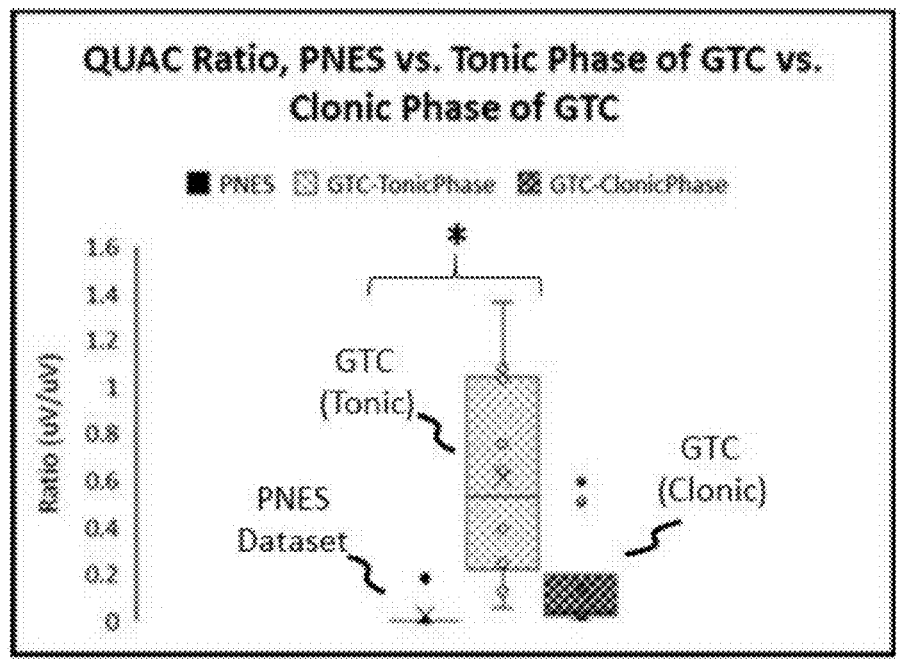
FIG. 13B shows additional QUAC data for GTC and PNES events.

The QUAC data for the ten suspected PNES and the ten GTC seizures is shown in FIG. 13A and FIG. 13B. As shown in FIG. 13A, where QUAC ratios were determined over the full length of both PNES and seizure events, QUAC ratios for PNES events is significantly lower (P<0.05) than for GTC seizure events. As shown in FIG. 13B, where QUAC ratios were determined over each of the tonic and clonic phases of detected GTC seizure events, QUAC ratios for PNES events were also lower than for the GTC seizure events. As shown in FIG. 13B, the differences were greater (P<0.05) when integration boundaries over the tonic phase were selected. Accordingly, EMG was found to provide similar results for detection of PNES as compared to techniques based on EEG analysis and verification by trained epileptologists. Thus, collection of EMG data may provide a useful alternative for detection of PNES and for diagnosis of patients who may be prone to suffering PNES. As described previously, EMG analysis is ideally suited for use in ambulatory methods for detection of seizures. Thus, EMG analysis provides a convenient way to collect large datasets over time and for detection of conditions such as PNES that may only manifest infrequently.

Although the methods and apparatus disclosed and their advantages have been described in detail, it should be understood that various changes, substitutions and alterations may be made herein without departing from the invention as defined by the appended claims. Moreover, the scope of the present application is not intended to be limited to the particular embodiments of the process, machine, manufacture, composition, or matter, means, methods and steps described in the specification. Use of the word "include," for example, should be interpreted as the word "comprising" would be, i.e., as open-ended. As one will readily appreciate from the disclosure, processes, machines, manufactures, compositions of matter, means, methods, or steps presently existing or later to be developed that perform substantially the same function or achieve substantially the same result as the corresponding embodiments described herein may be utilized. Accordingly, the appended claims are intended to include within their scope such processes, machines, manufactures, compositions of matter, means, methods or steps.

We claim:

1. A method for differentiating psychogenic non-epileptic seizure (PNES) events from generalized tonic-clonic (GTC) seizure events using electromyography (EMG) to identify patients having a PNES disorder, the method comprising:
    positioning an EMG detection unit including one or more EMG electrodes on or near a patient's skin over a muscle of the patient, the EMG detection unit suitable for daily monitoring of patient motor activity without requiring any associated wires or electrodes to the patient's head;
    collecting EMG signal data from said one or more EMG electrodes while the patient engages in normal daily living in the patient's home environment, said EMG signal data including at least one seizure-related event, the at least one seizure-related event being one of a generalized tonic-clonic seizure event or a PNES event;
    transforming either of the EMG signal data including said at least one seizure-related event or a portion thereof using one or more frequency transforms or wavelet transforms in order to produce transformed EMG data for said at least one seizure-related event;
    organizing said transformed EMG data for said at least one seizure-related event into a high frequency group of EMG signal data and a low frequency group of EMG signal data;
    wherein said high frequency group of EMG signal data includes data for a band of frequencies from about 120 Hz to about 400 Hz;
    wherein said low frequency group of EMG signal data includes data for a band of frequencies from about 6 Hz to about 70 Hz;
    determining a first integrated area for the high frequency group of EMG signal data and determining a second integrated area for the low frequency group of EMG signal data;
    determining whether a ratio between the first integrated area and the second integrated area meets a ratio threshold for distinguishing GTC seizure events from PNES events;
    classifying each of said at least one seizure-related event as either of a PNES event or a GTC seizure event based on whether said ratio meets said ratio threshold;
    wherein at least a first seizure-related event of the at least one seizure-related event is classified as PNES event; and
    generating a report based on how said at least one seizure-related event is classified, the report configured to indicate to a caregiver whether the patient may have a PNES disorder.

2. The method of claim 1 wherein said low frequency group of EMG signal data includes data for a band of frequencies from about 10 Hz to about 70 Hz.

3. The method of claim 1 wherein said low frequency group of EMG signal data includes data for a band of frequencies from about 20 Hz to about 70 Hz.

4. The method of claim 1 wherein said low frequency group of EMG signal data includes data for a band of frequencies from about 30 Hz to about 70 Hz.

5. The method of claim 1 wherein said high frequency group of EMG signal data includes data for a band of frequencies from about 150 Hz to about 400 Hz.

6. The method of claim 1, wherein said portion of said EMG signal data is based on processing said EMG signal data using one or more seizure-detection routines.

7. The method of claim 6, wherein said portion of said EMG signal data being an about 10-minute portion of said EMG signal data.

8. The method of claim 6 wherein said one or more seizure-detection routines are executed in real-time.

9. A method for identifying patients suffering from a psychogenic non-epileptic seizure (PNES) disorder, the method comprising:
    receiving electromyography (EMG) signal data including one or more seizure-related events, the one or more seizure-related events sorted so as to include either a GTC seizure event, a PNES seizure event, or a combination of both;
    collecting the EMG signal data using an EMG detection unit positioned on or near a patient's skin over a muscle of the patient, the EMG signal data being collected from the patient while the patient engages in daily living in the patient's home environment, the EMG detection unit suitable for daily monitoring of patient motor activity without requiring any associated wires or electrodes to the patient's head;
transforming said EMG signal data or a portion thereof using a frequency transform or a wavelet transform in order to produce transformed data for said one or more seizure-related events;
organizing said transformed data for each of said one or more seizure-related events into a high frequency group of EMG signal data and a low frequency group of EMG signal data;
wherein said high frequency group of EMG signal data includes data for a band of frequencies from about 120 Hz to about 400 Hz;
wherein said low frequency group of EMG signal data includes data for a band of frequencies from about 6 Hz to about 70 Hz;
determining a first integrated area for the high frequency group of EMG signal data and determining a second integrated area for the low frequency group of EMG signal data;
determining whether a ratio between the first integrated area and the second integrated area meets a ratio threshold for distinguishing PNES events from GTC seizure events;
classifying each of said seizure-related events as a PNES event or GTC seizure event based on whether said ratio meets said ratio threshold;
wherein at least a first seizure-related event of the one or more seizure-related events is classified as PNES event; and
identifying the patient as prone to suffering from PNES events based on whether said patient is found to have experienced one or more PNES events and sending a report to a caregiver, the report indicating that the patient may have a PNES disorder.

10. The method of claim 9, further comprising storing the collected EMG signal data in one or more medical databases, and wherein said EMG signal data is received by accessing said EMG signal data from said one or more medical databases.

11. The method of claim 10, wherein said EMG signal data comprises sorted data from said one or more medical databases, the sorted data including one or more data markings, said one or more data markings identifying that said seizure-related event is a seizure event of a certain type.

12. The method of claim 11, wherein said one or more data markings are provided by any of a physician, the patient, a local caregiver, and combinations thereof.

13. The method of claim 9, wherein said portion of said EMG signal data is based on processing said EMG signal data using one or more seizure-detection routines.

14. The method of claim 9, wherein said portion of said EMG signal data being an about 10-minute portion of data.

15. A system for classifying seizure events and differentiating psychogenic non-epileptic seizure (PNES) events from generalized tonic-clonic (GTC) seizure events using electromyography (EMG), the system comprising:
an EMG detection unit including one or more EMG electrodes configured for positioning on or near a patient's skin over a muscle of the patient, the EMG detection unit suitable for daily monitoring of patient motor activity without requiring any associated wires or electrodes to the patient's head;
a computer processor configured to:
receive EMG signal data including a seizure-related event;
transform the EMG signal data for said seizure-related event using a frequency transform or wavelet transform in order to produce transformed data for said seizure-related event;
organize said transformed data for said seizure-related event into a high frequency group of EMG signal data and a low frequency group of EMG signal data;
determine a first integrated area for the high frequency group of EMG signal data and determine a second integrated area for the low frequency group of EMG signal data;
wherein said high frequency group of EMG signal data includes data for a band of frequencies from about 120 Hz to about 400 Hz;
wherein said low frequency group of EMG signal data includes data for a band of frequencies from about 6 Hz to about 70 Hz;
determine whether a ratio between the first integrated area and the second integrated area meets a ratio threshold;
classify said seizure-related event as a PNES event based on whether said ratio meets said ratio threshold; and
generate a report based on the classifying of said seizure-related event, the report indicating to a caregiver whether a patient may have a PNES disorder.

16. The system of claim 15 further comprising:
one or more medical databases configured for storing said EMG signal data and sending said EMG signal data to said computer processor.

* * * * *